(12) United States Patent
Miyaki

(10) Patent No.: US 8,619,142 B2
(45) Date of Patent: Dec. 31, 2013

(54) ULTRASONIC OBSERVATION APPARATUS, OPERATION METHOD OF THE SAME, AND COMPUTER READABLE RECORDING MEDIUM

(75) Inventor: Hironaka Miyaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/601,094

(22) Filed: Aug. 31, 2012

(65) Prior Publication Data
US 2013/0113938 A1    May 9, 2013

Related U.S. Application Data

(63) Continuation of application No. PCT/JP2012/058786, filed on Mar. 27, 2012.

(30) Foreign Application Priority Data

Mar. 31, 2011 (JP) ................ 2011-080913

(51) Int. Cl.
G01S 15/89 (2006.01)

(52) U.S. Cl.
USPC .......................................... 348/163

(58) Field of Classification Search
USPC .......................... 348/61, 162, 163
See application file for complete search history.

(56) References Cited

U.S. PATENT DOCUMENTS

| | | |
|---|---|---|
| 2004/0039286 A1 | 2/2004 | Kuban et al. |
| 2004/0122326 A1 | 6/2004 | Nair et al. |
| 2004/0152983 A1 | 8/2004 | Vince et al. |
| 2005/0203405 A1 | 9/2005 | Tsujita |
| 2006/0241486 A1 | 10/2006 | Nair et al. |
| 2006/0241487 A1 | 10/2006 | Nair et al. |
| 2006/0253033 A1 | 11/2006 | Nair et al. |
| 2007/0160275 A1 | 7/2007 | Sathyanarayana |

(Continued)

FOREIGN PATENT DOCUMENTS

| | | |
|---|---|---|
| JP | 2005-253827 A | 9/2005 |
| JP | 2005-536289 A | 12/2005 |

(Continued)

OTHER PUBLICATIONS

International Search Report PCT/JP2012/058786 dated May 22, 2012.
Nair, A, et al. "Coronary Plaque Classification with Intravascular Ultrasound Radiofrequency Data Analysis", Circulation, Oct. 22, 2002, vol. 106, pp. 2200-2206.

(Continued)

Primary Examiner — Young Lee
(74) Attorney, Agent, or Firm — Scully, Scott, Murphy & Presser, PC

(57) ABSTRACT

An apparatus includes a unit that analyzes frequencies of an ultrasonic wave at a plurality of points to calculate a frequency spectrum of the points; a unit that approximates a portion included in a frequency band between a first frequency and a second frequency larger than the first frequency, by a polynomial, in the frequency spectrum of the points to extract first spectrum intensity which is a value of the polynomial in a third frequency included in a domain of the polynomial and second spectrum intensity which is a value of the polynomial in a fourth frequency different from the first to third frequencies, as a feature amount; and a unit that associates the first spectrum intensity, the second spectrum intensity, and/or a function of difference or ratio between the first and second spectrum intensity, to generate a feature amount image to indicate a distribution of the feature amount.

21 Claims, 21 Drawing Sheets
(1 of 21 Drawing Sheet(s) Filed in Color)

(56) References Cited

U.S. PATENT DOCUMENTS

| | | |
|---|---|---|
| 2007/0239007 A1 | 10/2007 | Silverman et al. |
| 2008/0051659 A1 | 2/2008 | Waki et al. |
| 2008/0287795 A1 | 11/2008 | Klingensmith et al. |

FOREIGN PATENT DOCUMENTS

| | | |
|---|---|---|
| JP | 2007-524431 A | 8/2007 |
| JP | 2009-523059 A | 6/2009 |
| WO | WO 2005/122906 A1 | 12/2005 |

OTHER PUBLICATIONS

Nair, A, et al. "Assessing Spectral Algorithms to Predict Atherosclerotic Plaque Composition with Normalized and Raw Intravascular Ultrasound Data", Ultrasound in Medicine & Biology, Oct. 1, 2001, vol. 27, No. 10, pp. 1319-1331.

Spencer, T., et al. Characterization of Atherosclerotic Plaque by Spectral Analysis of Intravascular Ultrasound: an In Vitro Methodology, Ultrasound in Medicine & Biology, Jan. 1, 1997, vol. 23, No. 2, pp. 191-203.

European Search Report dated Jul. 2, 2013 from corresponding European Application No. 12 76 5705.4.

| RECEPTION DEPTH (cm) | $f_{LOW}$ (MHz) | $f_{HIGH}$ (MHz) |
|---|---|---|
| 2 | 4 | 9 |
| 4 | 4 | 9 |
| 6 | 4 | 9 |
| 8 | 3.5 | 8 |
| 10 | 3 | 6.5 |
| 12 | 2.5 | 5 | ies of an ultrasonic wave at a plurality of points which are
ULTRASONIC OBSERVATION APPARATUS, OPERATION METHOD OF THE SAME, AND COMPUTER READABLE RECORDING MEDIUM

CROSS-REFERENCE TO RELATED APPLICATION

This application is a continuation of PCT international application Ser. No. PCT/JP2012/058786 filed on Mar. 27, 2012 which designates the United States, incorporated herein by reference, and which claims the benefit of priority from Japanese Patent Applications No. 2011-080913, filed on Mar. 31, 2011, incorporated herein by reference.

BACKGROUND OF THE INVENTION

1. Field of the Invention

The present invention relates to an ultrasonic observation apparatus used to observe tissue of a specimen using an ultrasonic wave, an operation method of an ultrasonic observation apparatus, and a computer readable recording medium.

2. Description of the Related Art

In the past, a technique called an ultrasonic elastography has been known as an examination technique of a breast cancer or the like using an ultrasonic wave (for example, see International Patent Publication No. 2005/122906). The ultrasonic elastography is a technique using the fact that a cancer in a living body or hardness of tumor tissue differs according to a progress state of a disease or a living body. In this technique, a strain amount or an elastic modulus of living tissue at an examination point is measured using an ultrasonic wave in a state in which the examination point is pressed from the outside, and a cross-sectional image is displayed as a measurement result.

SUMMARY OF THE INVENTION

An ultrasonic observation apparatus according to the present invention transmits an ultrasonic wave to a specimen and receives the ultrasonic wave reflected from the specimen. The ultrasonic observation apparatus includes: a frequency analyzing unit that analyzes frequencies of the ultrasonic wave at a plurality of points which are respectively positioned on a plurality of acoustic rays of the received ultrasonic wave and different from each other to calculate a frequency spectrum of each of the points; a feature amount extracting unit that approximates a portion included in a frequency band between a first frequency and a second frequency larger than the first frequency, by a polynomial, in the frequency spectrum of each of the points calculated by the frequency analyzing unit to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum of each of the points; and a feature amount image data generating unit that associates any one of (a) the first spectrum intensity, (b) the second spectrum intensity, and (c) a function of a difference or a ratio between the first spectrum intensity and the second spectrum intensity, with first visual information to generate a feature amount image which visually indicates a distribution of the feature amount.

An operation method of an ultrasonic observation apparatus according to the present invention, which transmits an ultrasonic wave to a specimen and receives the ultrasonic wave reflected from the specimen, includes: analyzing, by a frequency analyzing unit, frequencies of the ultrasonic wave at a plurality of points which are respectively positioned on a plurality of acoustic rays of the received ultrasonic wave and different from each other to calculate a frequency spectrum of each of the points; approximating, by a feature amount extracting unit, a portion included in a frequency band between a first frequency and a second frequency larger than the first frequency, by a polynomial, in the calculated frequency spectrum of each of the points to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum of each of the points; and associating, by a feature amount image data generating unit, any one of (a) the first spectrum intensity, (b) the second spectrum intensity, and (c) a function of a difference or a ratio between the first spectrum intensity and the second spectrum intensity, with first visual information to generate a feature amount image which visually indicates a distribution of the feature amount.

A non-transitory computer readable recording medium according to the present invention has an executable program stored thereon, wherein the program instructs a processor to perform: analyzing, by a frequency analyzing unit, frequencies of an ultrasonic wave at a plurality of points which are respectively positioned on a plurality of acoustic rays of the ultrasonic wave and different from each other to calculate a frequency spectrum of each of the points; approximating, by a feature amount extracting unit, a portion included in a frequency band between a first frequency and a second frequency larger than the first frequency, by a polynomial, in the calculated frequency spectrum of each of the points to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum of each of the points; and associating, by a feature amount image data generating unit, any one of (a) the first spectrum intensity, (b) the second spectrum intensity, and (c) a function of a difference or a ratio between the first spectrum intensity and the second spectrum intensity, with first visual information to generate a feature amount image which visually indicates a distribution of the feature amount.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Hereinafter, embodiments for carrying out the present invention (hereinafter, referred to as "embodiment") will be described with reference to the accompanying drawings.

First Embodiment

Figure 1:
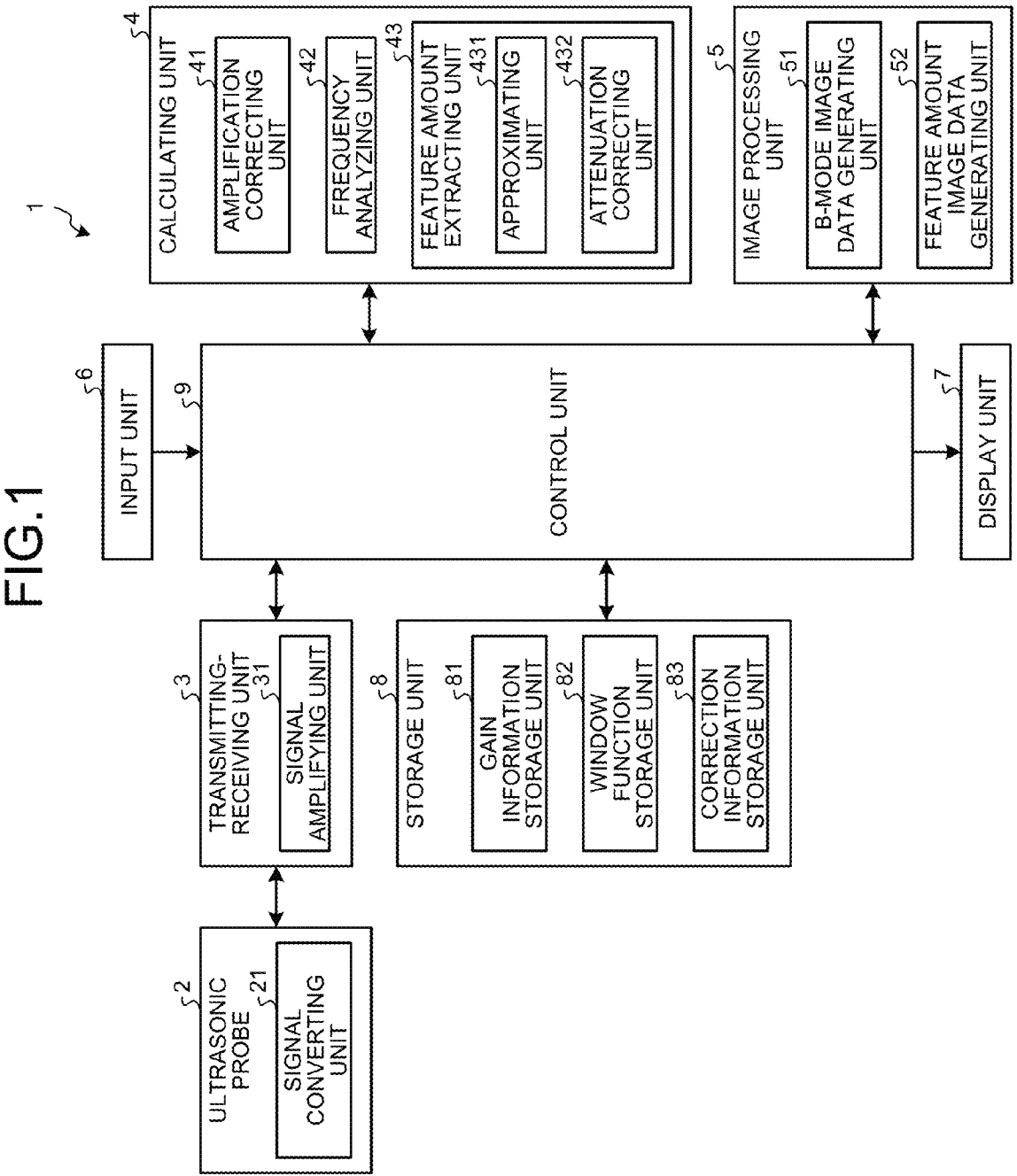
FIG. 1 is a block diagram illustrating a configuration of an ultrasonic observation apparatus according to a first embodiment of the present invention.

FIG. 1 is a block diagram illustrating a configuration of an ultrasonic observation apparatus according to a first embodiment of the present invention. An ultrasonic observation apparatus 1 illustrated in FIG. 1 is an apparatus used to observe a specimen using an ultrasonic wave.

The ultrasonic observation apparatus 1 includes an ultrasonic probe 2 that outputs an ultrasonic pulse to the outside and receives an ultrasonic echo reflected from the outside, a transmitting-receiving unit 3 that transmits/receives an electric signal to/from the ultrasonic probe 2, a calculating unit 4 that performs a predetermined calculation on an electric echo signal converted from the ultrasonic echo, an image processing unit 5 that generates image data corresponding to the electric echo signal converted from the ultrasonic echo, an input unit 6 that receives an input of a various kinds of information, a display unit 7 that is implemented using a display panel including a liquid crystal display (LCD) or an organic electroluminescence (EL) display and displays various kinds of information including an image generated by the image processing unit 5, a storage unit 8 that stores various kinds of information including information related to tissue characterization of a known specimen, and a control unit 9 that perform operation control of the ultrasonic observation apparatus 1.

In the first embodiment, the "tissue characterization" refers to any one of a cancer, an endocrinoma, a mucinous tumor, a normal tissue, a vascular channel, and the like. Further, when a specimen is a pancreas, a chronic pancreatitis, an autoimmune pancreatitis, and the like are included as the tissue characterization. This is similarly applied to the embodiment which will be described later.

The ultrasonic probe 2 includes a signal converting unit 21 that converts an electric pulse signal received from the transmitting-receiving unit 3 into an ultrasonic pulse (an acoustic pulse signal), and converts an ultrasonic echo reflected from an external specimen into an electric echo signal. The ultrasonic probe 2 may mechanically scan an ultrasonic transducer or may electronically scan a plurality of ultrasonic transducers.

The transmitting-receiving unit 3 is electrically connected with the ultrasonic probe 2, transmits a pulse signal to the ultrasonic probe 2, and receives an echo signal which is a reception signal from the ultrasonic probe 2. Specifically, the transmitting-receiving unit 3 generates a pulse signal based on a waveform and a transmission timing which are set in advance, and transmits the generated pulse signal to the ultrasonic probe 2.

Figure 2:
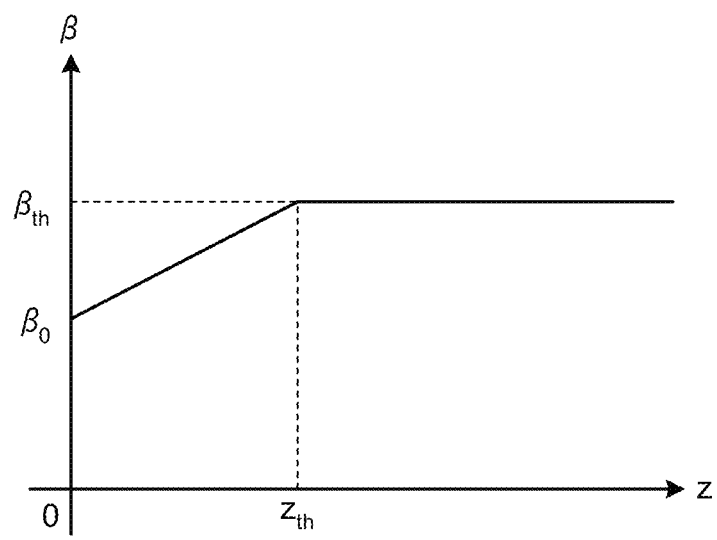
FIG. 2 is a diagram illustrating a relation between a reception depth and a gain in an amplifying process performed by a signal amplifying unit of the ultrasonic observation apparatus according to the first embodiment of the present invention.

The transmitting-receiving unit 3 includes a signal amplifying unit 31 that amplifies an echo signal. Specifically, the signal amplifying unit 31 performs sensitivity time control (STC) correction in which an echo signal is amplified with a higher gain as the echo signal has a larger reception depth. FIG. 2 is a diagram illustrating a relation between the reception depth and the gain of the echo signal. A reception depth z illustrated in FIG. 2 refers an amount of an ultrasonic wave calculated based on a time elapsed from a reception start time. As illustrated in FIG. 2, when the reception depth z is smaller than the threshold value $z_{th}$, the gain β linearly increases from $β_0$ to $β_{th}$ (>$β_0$) as the reception depth z increases. However, the reception depth z is the threshold value $z_{th}$ or more, and the gain β has a constant value $β_{th}$. The threshold value $z_{th}$ is set to a value in which an ultrasonic signal received from a specimen is almost attenuated and so a noise is dominant. More generally, the gain β preferably monotonically increases with the increase in the reception depth z when the reception depth z is smaller than the threshold value $z_{th}$.

The transmitting-receiving unit 3 executes processing such as filtering on the echo signal amplified by the signal amplifying unit 31, generates a digital radio frequency (RF) signal by performing A/D conversion on the processed signal, and outputs the digital RF signal. In addition, when a plurality of ultrasonic transducers are electronically scanned by the ultrasonic probe 2, the transmitting-receiving unit 3 has a multi-channel circuit for beam synthesis corresponding to a plurality of ultrasonic transducers.

The calculating unit 4 includes an amplification correcting unit 41 that performs amplification correction, by which a gain becomes constant regardless of the reception depth, on the digital RF signal output by the transmitting-receiving unit 3, a frequency analyzing unit 42 that calculates a frequency spectrum (power spectrum) by executing fast Fourier transform (FFT) on the digital RF signal that has been subjected to the amplification correction and performing frequency analysis, and a feature amount extracting unit 43 that extracts a feature amount of a frequency spectrum by performing an approximate process and a correction process of reducing contribution of an attenuation of an ultrasonic wave that depends on the reception depth and the frequency of the ultrasonic wave on the frequency spectrum calculated by the frequency analyzing unit 42.

Figure 3:
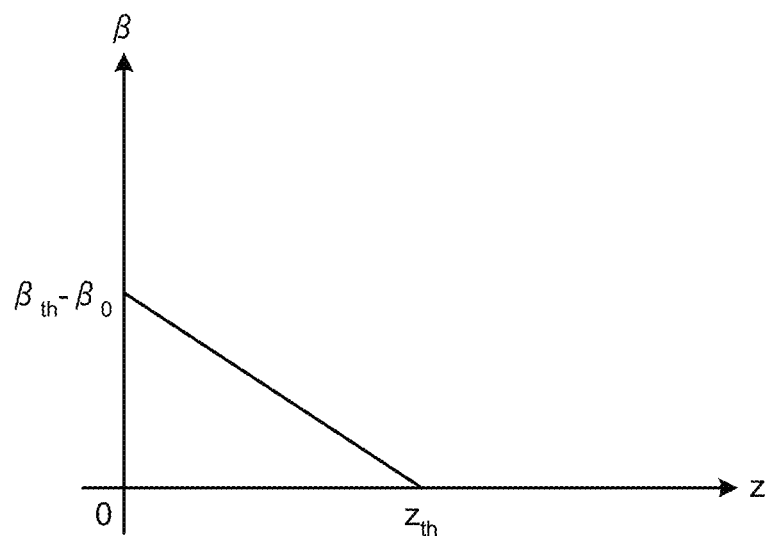
FIG. 3 is a diagram illustrating a relation between a reception depth and a gain in an amplifying process performed by an amplification correcting unit of the ultrasonic observation apparatus according to the first embodiment of the present invention.

FIG. 3 is a diagram a relation between the reception depth and the gain in the amplifying process performed by the amplification correcting unit 41. As illustrated in FIG. 3, the gain in the amplifying process performed by the amplification correcting unit 41 has a maximum value $β_{th}-β_0$ when the reception depth z is zero (0), linearly decreases until the reception depth z reaches the threshold value $z_{th}$ from zero, and becomes zero when the reception depth z is the threshold value $z_{th}$ or more. The amplification correcting unit 41 can perform the amplification correction on the digital RF signal based on the gain decided by the above-described way, offset influence of STC correction in the signal amplifying unit 31, and output a signal of the gain $β_{th}$. Of course, the relation between the reception depth z and the gain β performed by the amplification correcting unit 41 differs according to the relation between the reception depth and the gain in the signal amplifying unit 31.

The frequency analyzing unit 42 performs a fast Fourier transform on an FFT data group having a predetermined volume of data for each acoustic ray (line data) to calculate a frequency spectrum at a point (a data position) on the acoustic ray. Depending on the tissue characterization of a specimen, the frequency spectrum demonstrates a different tendency. That is because of the fact that a frequency spectrum has a correlation with the size, the density, and the acoustic impedance of the specimen that serves as a scatterer which scatters the ultrasonic sound waves.

Figure 4:
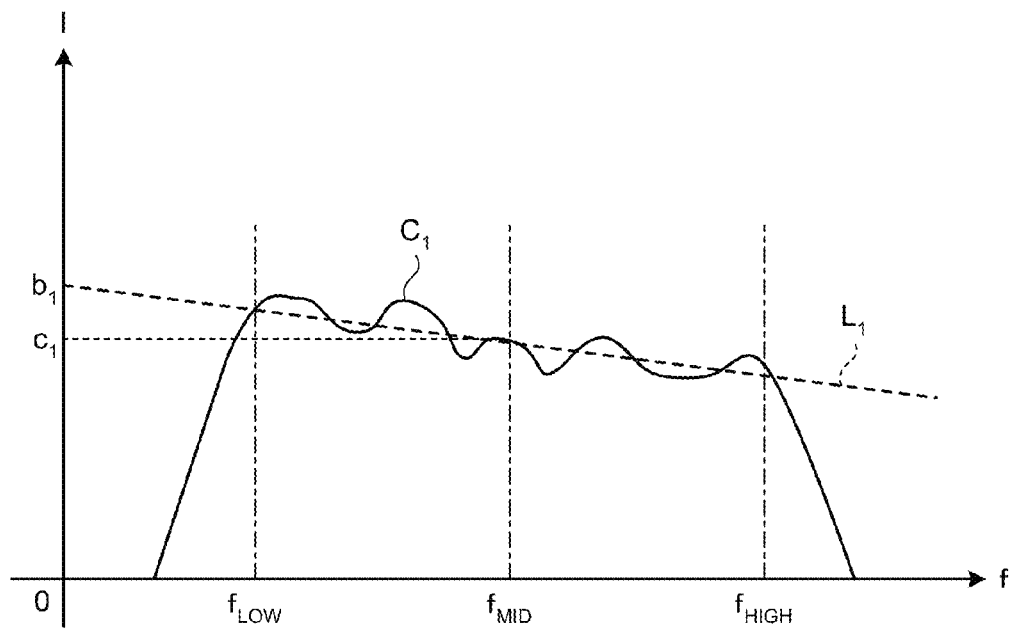
FIG. 4 is a diagram illustrating an example (a first example) of a frequency spectrum calculated by a frequency analyzing unit of the ultrasonic observation apparatus according to the first embodiment of the present invention.

FIG. 4 is a diagram illustrating an example of a frequency spectrum calculated by the frequency analyzing unit 42. In FIG. 4, a horizontal axis f represents the frequency, and a vertical axis I represents the intensity. In a frequency spectrum curve $C_1$ illustrated in FIG. 4, a lower limit frequency (a first frequency) $f_{LOW}$ and an upper limit frequency (a second frequency) $f_{HIGH}$ of the frequency spectrum are parameters which are decided based on the frequency band of the ultrasonic probe 2, the frequency band of the pulse signal transmitted by the transmitting-receiving unit 3, and the like, and, for example, the lower limit frequency $f_{LOW}$ and the upper limit frequency $f_{HIGH}$ are 3 MHz and 10 MHz, respectively. In the first embodiment, a curve and a straight line include a set of discrete points. This point is similarly applied in an embodiment which will be described later.

The feature amount extracting unit 43 calculates a polynomial approximation for a portion, which is included in a frequency band between a first frequency and a second frequency larger than the first frequency in the frequency spectrum of each point calculated by the frequency analyzing unit 42, to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum in each point. The details of the third and fourth frequencies and the first and second spectrum intensity will be described later.

Specifically, the feature amount extracting unit 43 includes an approximating unit 431 that calculates a pre-correction feature amount before an attenuation correction process is performed by performing the approximate process on the frequency spectrum calculated by the frequency analyzing unit 42, and an attenuation correcting unit 432 that extracts a feature amount by performing the attenuation correction process on the pre-correction feature amount approximated by the approximating unit 431.

The approximating unit 431 performs linear approximation with respect to the frequency spectrum by means of regression analysis so as to extract pre-correction feature amount that characterizes the approximated linear expression. Specifically, the approximating unit 431 calculates a slope $a_1$ and the intercept $b_1$ of the linear expression by the regression analysis, as well as calculates a specific spectrum intensity $c_1$ in a specific frequency (the third frequency) within the frequency band in the frequency spectrum as the pre correction feature amount. Here, the "spectrum intensity" represents any one of parameters such as a voltage, power, sound pressure, and acoustic energy. In the first embodiment, the approximating unit 431 calculates spectrum intensity (Mid-band fit) $c_1$ ($=a_1 f_{MID}+b_1$) in a central frequency $f_{MID}$ ($=(f_{LOW}+f_{HIGH})/2$) as the specific spectrum intensity $c_1$.

A straight line $L_1$ illustrated in FIG. 4 refers to a regression line corresponding to the linear expression having the pre-correction feature amount $a_1$, $b_1$, and $c_1$ which the approximating unit 431 has extracted from the frequency spectrum curve $C_1$. Here, the intercept $b_1$ corresponds to the spectrum intensity in which the frequency f is zero (0). Hereinafter, the frequency f (=0) corresponding to the intercept $b_1$ is referred to as the fourth frequency. Further, the approximate polynomial calculated by the feature amount extracting unit 43 is not limited to the linear expression and may be a quadratic or more approximate polynomial.

Among the three feature amounts, the slope $a_1$ has a correlation with the size of a scatterer of an ultrasonic wave, and as the size of the scatterer increases, the value of the slope decreases. In addition, the intercept $b_1$ has a correlation with the size of a scatterer, an acoustic impedance ratio of a scatterer and a peripheral material, and the number of scatterers per unit volume. The spectrum intensity (hereinafter, referred to simply as "central frequency intensity") $c_1$ in the central frequency $f_{MID}$ is an indirect parameter calculated based on the slope $a_1$ and the intercept $b_1$, and provides the spectrum intensity in the center of the effective frequency band. For this reason, the central frequency intensity $c_1$ has a correlation with luminance of a B-mode image obtained by converting an amplitude of an echo signal into luminance in addition to the size of a scatterer, an acoustic impedance ratio of a scatterer and a peripheral material, and the number of scatterers per unit volume.

The feature amount is not limited to $a_1$, $b_1$, and $c_1$. For example, it is possible to set an arbitrary frequency f' that satisfies $f_{LOW} < f' < f_{HIGH}$ instead of $f=f_{MID}$ as the third frequency and employ the spectrum intensity in the third frequency f' as the feature amount. Further, it is possible to set an arbitrary frequency f" that satisfies $f" < f_{LOW}$ or $f" > f_{HIGH}$ instead of f=0 as the fourth frequency and employ the spectrum intensity in the fourth frequency f" as the feature amount.

Next, correction performed by the attenuation correcting unit 432 will be described. An attenuation amount A of an ultrasonic wave is represented by the following formula:

$$A = 2\alpha z f \quad (1),$$

where $\alpha$ represents an attenuation rate, z represents a reception depth of an ultrasonic wave, and f represents the frequency. As can be seen from Formula (1), the attenuation amount A is in proportion to the frequency f. In case of a living body, a concrete value of the attenuation rate $\alpha$ is 0 to 1.0 (dB/cm/MHz), and preferably 0.3 to 0.7 (dB/cm/MHz), and decided according to the type of observation target. For example, when an observation target is a pancreas, $\alpha$ is decided as 0.6 (dB/cm/MHz). In addition, in the first embodiment, the value of the attenuation rate $\alpha$ may be changed according to an input from the input unit 6.

The attenuation correcting unit 432 corrects the pre-correction feature amount (the slope $a_1$, the intercept $b_1$, and the central frequency intensity $c_1$) extracted by the approximating unit 431 as follows.

$$a = a_1 + 2\alpha z \quad (2)$$

$$b = b_1 \quad (3)$$

$$c = c_1 + 2\alpha z f_{MID} (= af_{MID} + b) \quad (4)$$

As can be seen from Formulas (2) and (4), in the attenuation correction which the attenuation correcting unit 432 performs on the slope $a_1$ and the central frequency intensity $c_1$, as the reception depth z of the ultrasonic wave increases, the correction amount increases. Further, as can be seen from Formula (3), the attenuation correction which the attenuation correcting unit 432 performs on the intercept $b_1$ is identity transformation. It is because the intercept $b_1$ is a frequency component corresponding to the frequency f (=0) and thus not attenuated.

Figure 5:
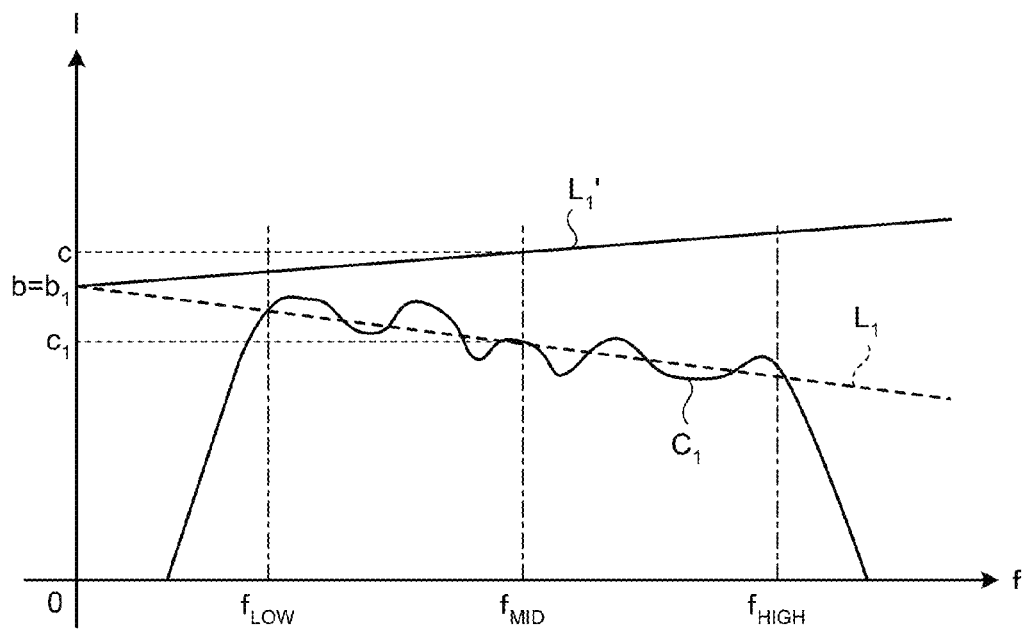
FIG. 5 is a diagram illustrating a new straight line decided based on a feature amount after an attenuation correction is performed on a feature amount associated with a straight line illustrated in FIG. 4.

FIG. 5 is a diagram illustrating a straight line decided based on a feature amount after the attenuation correction is performed on the feature amount associated with the straight line $L_1$ illustrated in FIG. 4. A straight line $L_1'$ illustrated in FIG. 5 is represented by the following formula:

$$I = af + b = (a_1 + 2\alpha Z)f + b_1 \quad (5)$$

As can be seen from Formula (5), the straight line $L_1'$ is larger ($a > a_1$) in the slope than, equal ($b = b_1$) in the intercept to, and larger ($c > c_1$) in the central frequency intensity than the straight line $L_1$.

The image processing unit 5 includes a B-mode image data generating unit 51 that generates B-mode image data based on an echo signal and a feature amount image data generating unit 52 that generates feature amount image data which indicates visual information corresponding to a feature amount of a frequency spectrum.

The B-mode image data generating unit 51 generates B-mode image data by performing signal processing on a digital signal using known techniques such as a band pass filter, a logarithmic conversion, a gain process, and a contrast process and performing data interleaving corresponding to a data step width decided according to a display range of an image in the display unit 7.

The feature amount image data generating unit 52 assigns an absolute value |b−c| of a difference (hereinafter, referred to as an "intensity difference") between the intercept b (the first spectrum intensity) and the central frequency intensity c (the second spectrum intensity) to a hue (first visual information) and assigns the intercept b or the central frequency intensity c to brightness and/or chroma (the second visual information) to generate feature amount image data including a feature amount image which visually indicates the distribution of the feature amounts. The reason of the association will be described with reference to FIGS. 6A to 9.

Figure 6A:
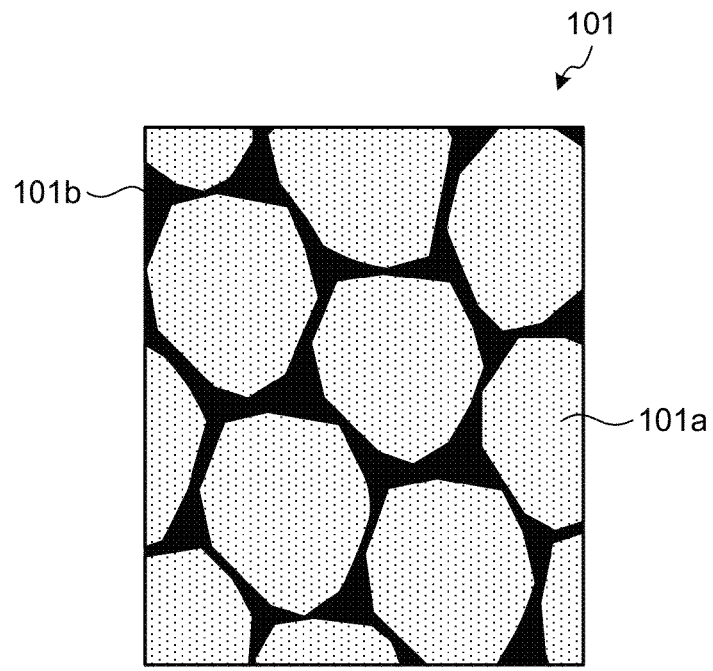
FIG. 6A is a diagram schematically illustrating an example in which an observation target is normal tissue.
Figure 6B:
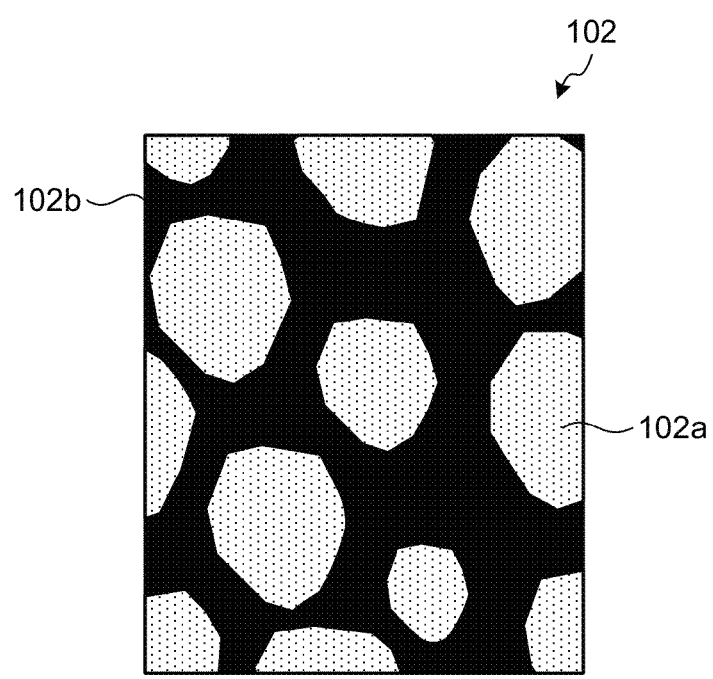
FIG. 6B is a diagram schematically illustrating an example in which an observation target is abnormal tissue.

FIGS. 6A and 6B are diagrams schematically illustrating two regions that differ in the size of a scatterer in the same tissue. Specifically, FIG. 6A is a diagram illustrating normal tissue, and FIG. 6B is a diagram illustrating tissue including abnormality such as an inflammation or a tumor. A tissue 101 illustrated in FIG. 6A includes a real tissue 101a (indicated by dots) such as a lobule and a connective tissue 101b (indicated by a dark portion) that connects fibrae with each other. Similarly, a tissue 102 illustrated in FIG. 6B includes a real tissue 102a (indicated by dots) and a connective tissue 102b (indicated by a dark portion). Here, when FIG. 6A is compared with FIG. 6B, the real tissue 101a is generally larger than the real tissue 102a. It can be interpreted as meaning that, for example, a part of the real tissue 101a is replaced with a fibra and thus its volume is reduced.

Figure 7:
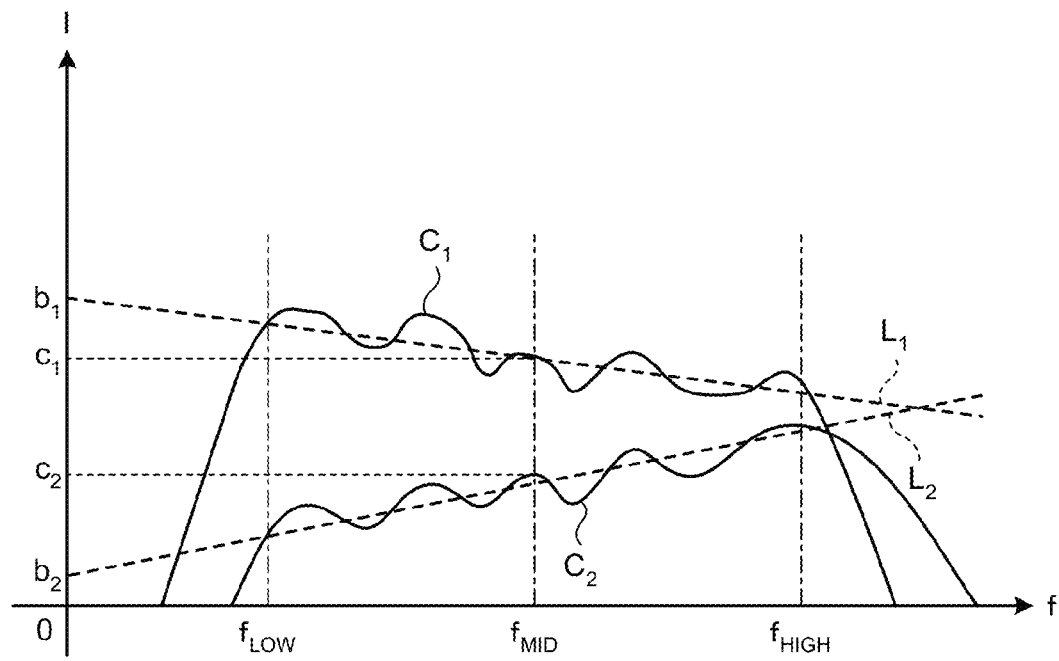
FIG. 7 is a diagram for describing that a frequency spectrum changes according to the size of a scatterer.

Generally, an ultrasonic wave is mainly scattered in the boundary between the real tissue and the connective tissue. For this reason, when the real tissue serving as a scatterer is small, a ratio of a transmitted wave that transmits tissue increases, and thus intensity of a backscattered wave decreases. FIG. 7 is a diagram illustrating this status. In FIG. 7, the frequency spectrum curves $C_1$ and $C_2$ are spectrum curves which differ in the size of a scatterer. Specifically, the scatterer corresponding to the frequency spectrum curve $C_1$ is larger than the scatterer corresponding to the frequency spectrum curve $C_2$. In this case, when the straight line $L_1$ obtained by approximating the frequency spectrum curve $C_1$ is compared with the straight line $L_2$ obtained by approximating the frequency spectrum curve $C_2$, the straight line $L_2$ is larger in the absolute value $|b-c|$ of the intensity difference than the straight line $L_1$ ($|b_1-c_1|<|b_2-c_2|$). In addition, the straight line $L_2$ is smaller in the intercept b and the central frequency intensity c than the straight line $L_1$ ($b_1>b_2$, $c_1>c_2$).

Figure 8:
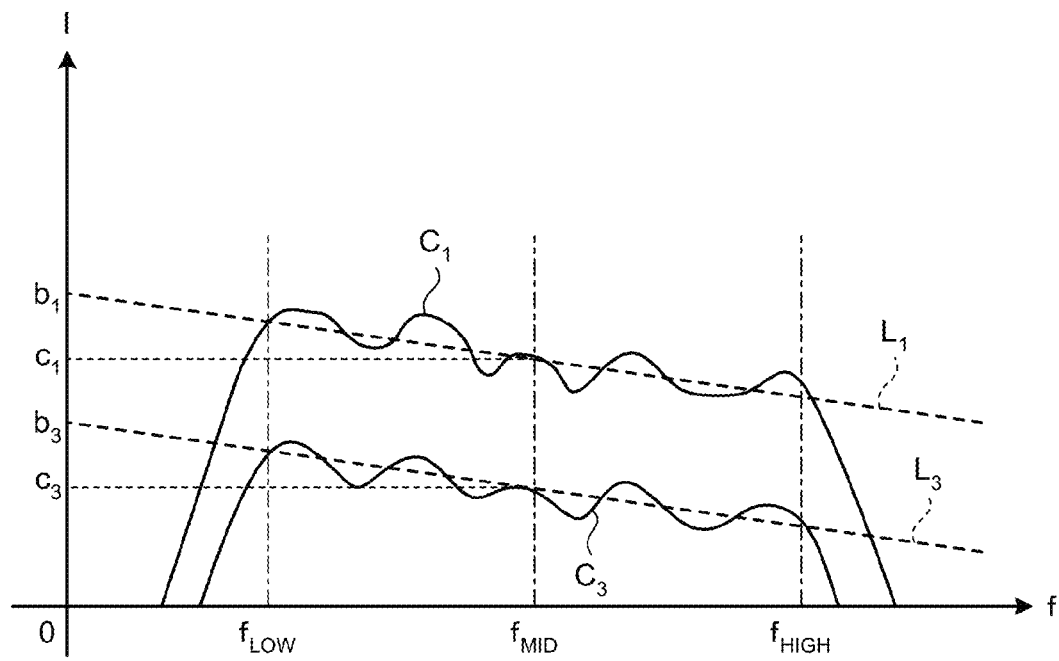
FIG. 8 is a diagram for describing a difference between frequency spectrums of tissues which are the same in the size of a scatterer as each other but differ in an acoustic impedance ratio or the number of scatterers per unit volume from each other.

FIG. 8 is a diagram illustrating frequency spectrums of two tissues which are almost the same in the size of a scatterer as each other but differ in the acoustic impedance ratio in the boundary between the scatterer and its peripheral material (hereinafter, referred to simply as a "acoustic impedance ratio") or the number of scatterers per unit volume (hereinafter, referred to as "density of scatterers") from each other. In FIG. 8, the frequency spectrum curve $C_3$ is smaller in the acoustic impedance ratio or the density of scatterers than the frequency spectrum curve $C_1$. Here, when the straight line $L_1$ obtained by approximating the frequency spectrum curve $C_1$ is compared with the straight line $L_3$ obtained by approximating the frequency spectrum curve $C_3$, the straight line $L_1$ is almost equal in the absolute value $|b-c|$ of the intensity difference the straight line $L_3$ ($|b_1-c_1|\approx|b_2-c_2|$). In addition, the straight line $L_3$ is smaller in the intercept b and the central frequency intensity c than the straight line $L_1$ ($b_1>b_3$, $c_1>c_3$).

Based on the description made with reference to FIGS. 7 and 8, it is possible to distinguish tissues that differ in the size of a scatterer and tissues that differ in the acoustic impedance ratio or the density of scatterers from each other using the absolute value $|b-c|$ of the intensity difference.

Figure 9:
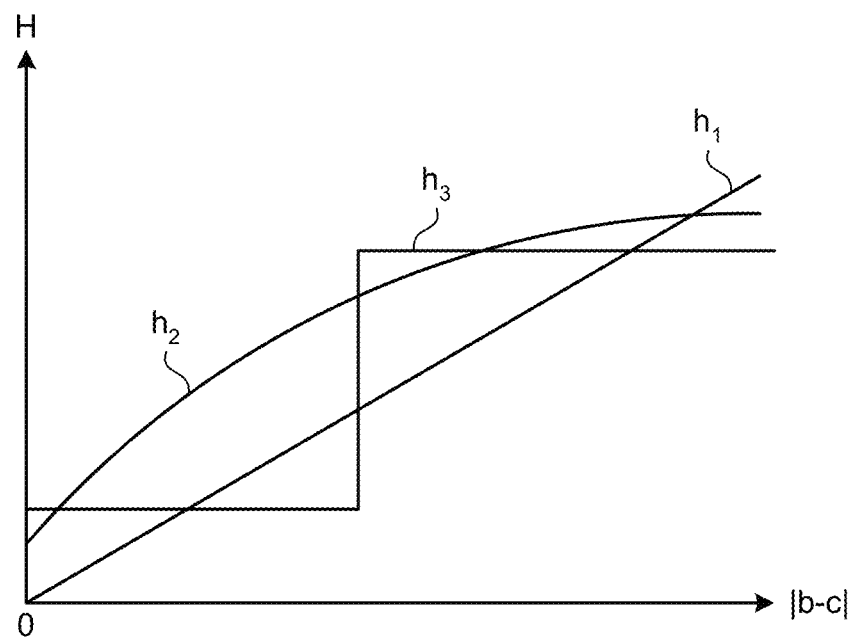
FIG. 9 is a diagram illustrating a relation between an absolute value of an intensity difference of spectrum intensity and a hue which the ultrasonic observation apparatus according to the first embodiment of the present invention assigns to a feature amount image.

FIG. 9 is a diagram illustrating an example in which a hue to be assigned in the feature amount image changes according to the absolute value of the intensity difference. A straight line $h_1$ illustrated in FIG. 9 represents an example in which a hue H is in a linear relation with the absolute value $|b-c|$ of the intensity difference. A curve $h_2$ illustrated in FIG. 9 represents an example in which the hue H is represented by a quadratic function of the absolute value $|b-c|$ of the intensity difference. Further, a step-like curve $h_3$ illustrated in FIG. 9 represents an example in which the hue H is binarized according to the absolute value $|b-c|$ of the intensity difference. Further, the hue H may be a function of a ratio (an intensity ratio) b/c of the intercept b and the central frequency intensity c. In addition, the hue H may be multi-valued in the form of a step according to the absolute value $|b-c|$ of the intensity difference.

Next, the reason of associating the intercept b or the central frequency intensity c with brightness or chroma will be described. Generally, in an ultrasonic image, it is known that in a vascular channel and a noise region, the intercept b and the central frequency intensity c decrease. For this reason, when low brightness or chroma is associated with a region which is low in the intercept b or the central frequency intensity c, it is possible to display a vascular channel and noise in an unrecognizable form (black or gray) different from a real tissue.

As can be understood from the reason for the association described above, in the feature amount image generated by the feature amount image data generating unit 52, regions which differ in the size of a scatterer are displayed in different hues. Further, in the feature amount image, regions which are equal in the size of a scatterer but differ in the acoustic impedance ratio or the density of scatterers is displayed in almost the same hue but at different brightness or chroma.

Next, the configuration of the ultrasonic observation apparatus 1 will be described. The input unit 6 is implemented using an interface such as a keyboard, a mouse, and a touch panel. The input unit 6 receives an input of information designating a region (hereinafter, referred to as a "region of interest") of an image in which the user of the ultrasonic observation apparatus 1 who has observed an image generated by the image processing unit 5 is interested.

The storage unit 8 includes a gain information storage unit 81 that stores information of a gain to which the signal amplifying unit 31 and the amplification correcting unit 41 refer at the time of the amplifying process, a window function storage unit 82 that stores a window function used when the frequency analyzing unit 42 performs a frequency analysis process, and a correction information storage unit 83 that stores correction information to which the attenuation correcting unit 432 refers at the time of execution of processing.

The gain information storage unit 81 stores the relation between the reception depth and the gain illustrated in FIGS. 2 and 3. The window function storage unit 82 stores at least one of window functions such as Hamming, Hanning, and Blackman. The correction information storage unit 83 stores information related to conversion of Formulas (2) to (4).

The storage unit 8 is implemented using read only memory (ROM) in which an operation program of the ultrasonic observation apparatus 1, a program to activate a predetermined operating system (OS), or the like is stored in advance and random access memory (RAM) in which a calculation parameter or data of each process is stored.

The control unit 9 is implemented using a central processing unit (CPU) having calculation and control functions. The control unit 9 controls the ultrasonic observation apparatus 1 in general by reading information stored in the storage unit 8 and various kinds of programs including an operation program of the ultrasonic observation apparatus from the storage unit 8 and executing various kinds of calculation processes related to an operation method of the ultrasonic observation apparatus 1.

In addition, the operation program of the ultrasonic observation apparatus 1 may be recorded in a computer readable recording medium such as a hard disk, a flash memory, a CD-ROM, a DVD-ROM, or a flexible disk and widely distributed.

Figure 10:
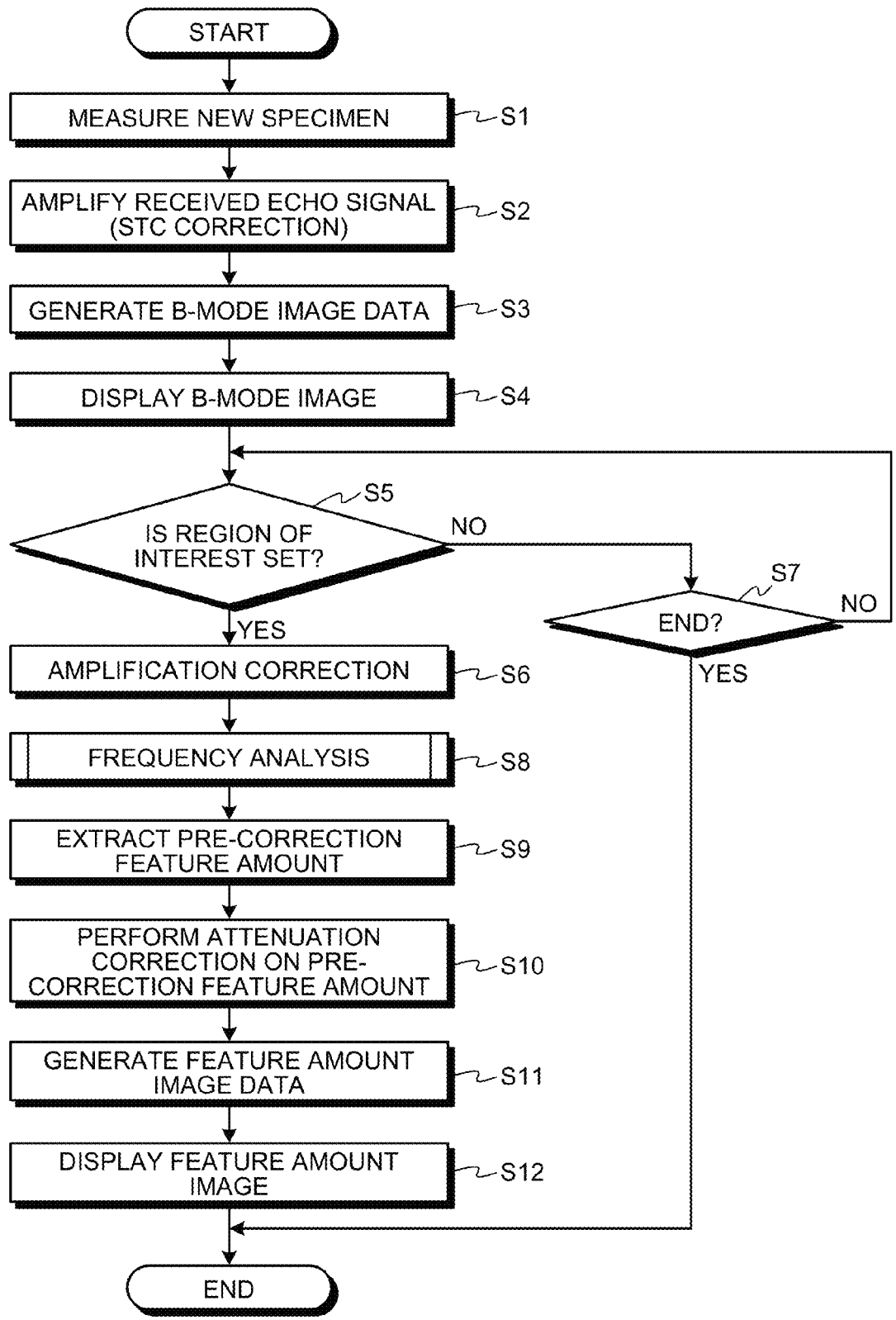
FIG. 10 is a flowchart illustrating a processing outline of the ultrasonic observation apparatus according to the first embodiment of the present invention.

FIG. 10 is a flowchart illustrating a processing outline of the ultrasonic observation apparatus 1 with the above-described configuration. In FIG. 10, first the ultrasonic observation apparatus 1 measures a new specimen through the ultrasonic probe 2 (step S1).

Next, the signal amplifying unit 31 that has received an echo signal from the ultrasonic probe 2 amplifies the echo signal (step S2). Here, the signal amplifying unit 31 performs the amplification based on the relation between the gain and the reception depth illustrated in FIG. 2.

Thereafter, the B-mode image data generating unit 51 generates B-mode image data using the echo signal for the B-mode image output from the transmitting-receiving unit 3 (step S3).

Figure 11:
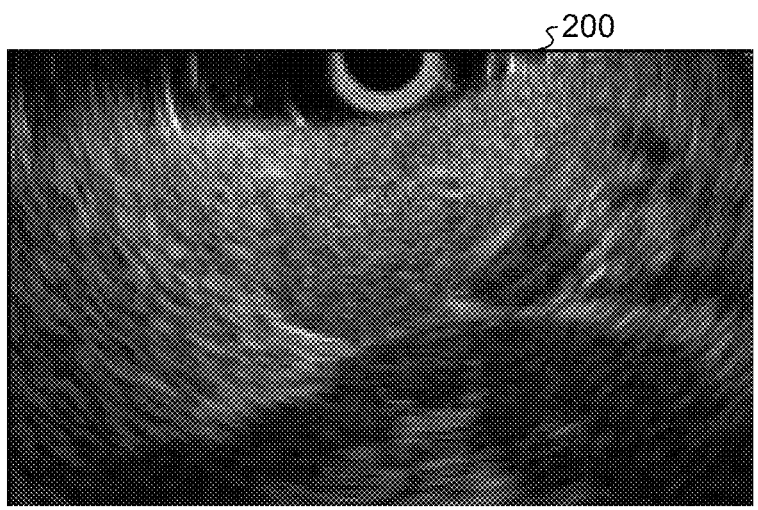
FIG. 11 is a diagram illustrating a display example of a B-mode image in a display unit of the ultrasonic observation apparatus according to the first embodiment of the present invention.

Next, the control unit 9 performs control such that the B-mode image corresponding to the B-mode image data generated by the B-mode image data generating unit 51 is displayed on the display unit 7 (step S4). FIG. 11 is a diagram illustrating a display example of the B-mode image in the display unit 7. A B-mode image 200 illustrated in FIG. 11 is a gray scale image in which values of R (red), G (green), and B (blue) which are variables of an RGB colorimetric system are matched.

Thereafter, if a region of interest is set through the input unit 6 (Yes in step S5), the amplification correcting unit 41 performs correction on a signal output from the transmitting-receiving unit 3 such that a gain becomes constant regardless of a reception depth (step S6). Here, the amplification correcting unit 41 performs the amplification correction process based on the relation between the gain and the reception depth illustrated in FIG. 3. A region corresponding to the entire B-mode image may be set as a region of interest. In this case, instructions to display the feature amount image data also function as setting instructions of a region of interest.

However, if the region of interest is not set (No in step S5) and instructions to end the process are input through the input unit 6 (Yes in step S7), the ultrasonic observation apparatus 1 ends the process. However, if the region of interest is not set (No in step S5) and the instructions to end the process are not input through the input unit 6 (No in step S7), the ultrasonic observation apparatus 1 causes the process to return to step S5.

After step S6, the frequency analyzing unit 42 performs the frequency analysis through the FFT calculation and calculates a frequency spectrum (step S8). In step S8, an entire region of an image may be set as a region of interest.

Figure 12:
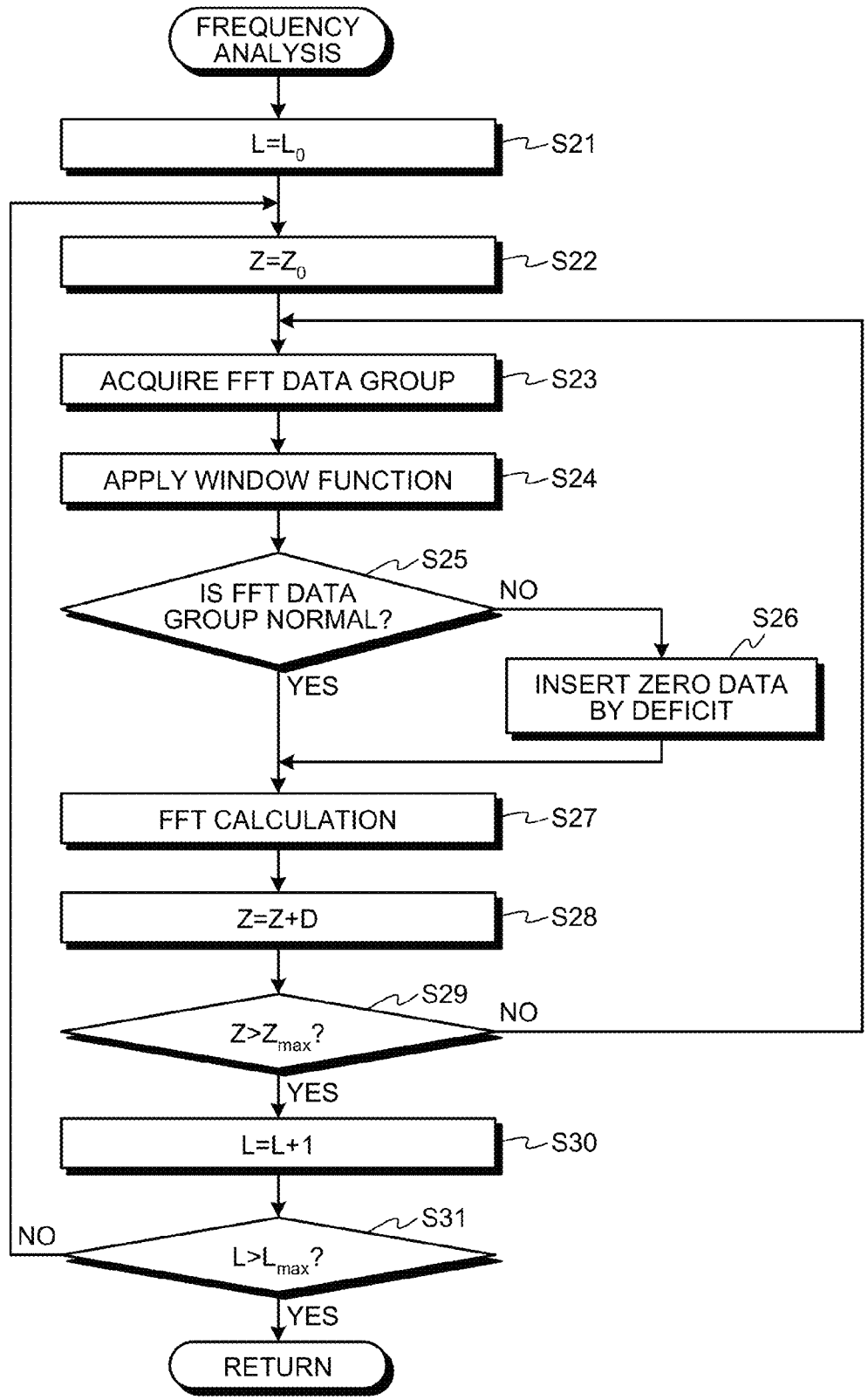
FIG. 12 is a flowchart illustrating an outline of a process performed by the frequency analyzing unit of the ultrasonic observation apparatus according to the first embodiment of the present invention.

Here, the process (step S8) performed by the frequency analyzing unit 42 will be described in detail with reference to a flowchart of FIG. 12. First, the frequency analyzing unit 42 sets an acoustic ray number L of an acoustic ray initially used as an analysis target to an initial value $L_0$ (step S21). For example, the initial value $L_0$ may be assigned to an acoustic ray initially received by the transmitting-receiving unit 3 or may be assigned to an acoustic ray corresponding to either of right and left boundary positions of the region of interest set through the input unit 6.

Figure 13:
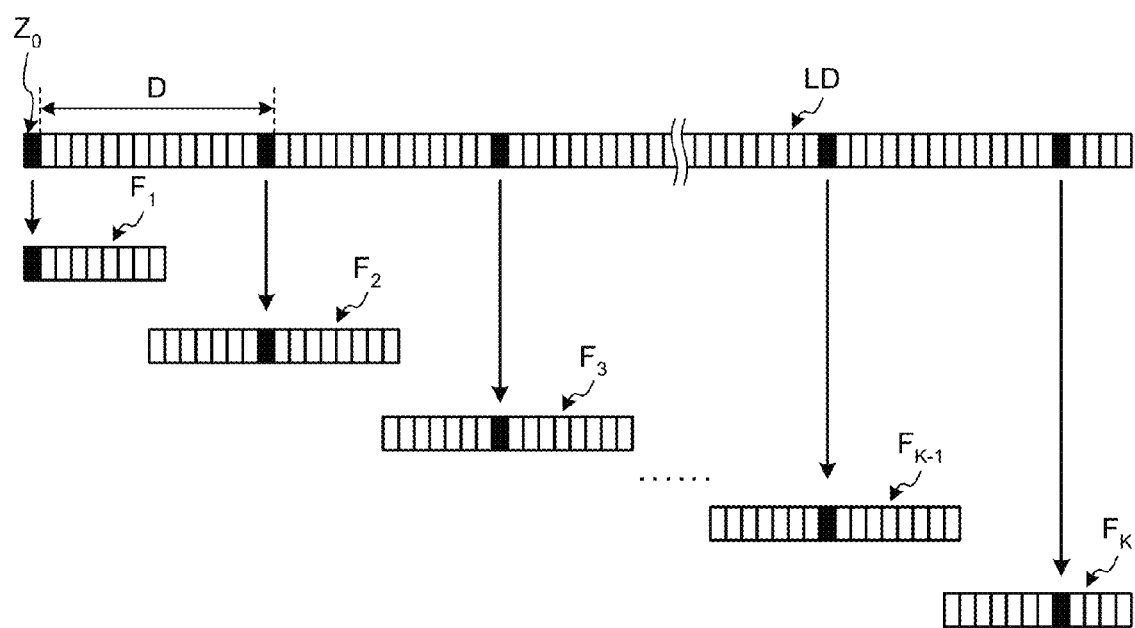
FIG. 13 is a diagram schematically illustrating a data array of one acoustic ray.

Next, the frequency analyzing unit 42 calculates frequency spectrums of all of a plurality of points (data positions) set on one acoustic ray. First, the frequency analyzing unit 42 sets an initial value $Z_0$ of a data position Z (which corresponds to a reception depth) representing a series of data groups (FFT data groups) acquired for FFT calculation (step S22). FIG. 13 is a diagram schematically illustrating a data array of one acoustic ray. In an acoustic ray LD illustrated in FIG. 13, a white or black rectangle means one data. The acoustic ray LD is discretized at time intervals corresponding to a sampling frequency (for example, 50 MHz) in A/D conversion performed by the transmitting-receiving unit 3. FIG. 13 illustrates an example in which first data of the acoustic ray LD is set as an initial value $Z_0$ of the data position Z. FIG. 13 is merely an example, and the position of the initial value $Z_0$ can be arbitrarily set. For example, a data position Z corresponding to an upper end position of a region of interest may be set as the initial value $Z_0$.

Thereafter, the frequency analyzing unit 42 acquires the FFT data group of the data position Z (step S23), and applies the window function stored in the window function storage unit 82 to the acquired FFT data group (step S24). As described above, by applying the window function to the FFT data group, it is possible to prevent the FFT data group from being discontinuous in the boundary and thus prevent generation of an artifact.

Next, the frequency analyzing unit 42 determines whether or not the FFT data group of the data position Z is a normal data group (step S25). The FFT data group needs to have data which is equal in number to data of a power of 2. Hereinafter, the number of data of the FFT data group is referred to as $2^n$ (n is a positive integer). Here, what the FFT data group is normal means that the data position Z is a $2^{n-1}$-th data position from the front in the FFT data group. In other words, what the FFT data group is normal means that data which is equal in number to $2^{n-1}-1$ (=N) exists ahead of the data position Z, and data which is equal in number to $2^{n-1}$ (=M) exists behind the data position Z. In the example illustrated in FIG. 13, n is 4 (N=7, M=8), and FFT data groups $F_2$, $F_3$, and $F_{K-1}$ are normal, but FFT data groups $F_1$ and $F_K$ are abnormal.

Here, when it is determined in step S25 that the FFT data group of the data position Z is normal (Yes in step S25), the frequency analyzing unit 42 causes the process to proceed to step S27.

However, when it is determined in step S25 that the FFT data group of the data position Z is not normal (No in step S25), the frequency analyzing unit 42 inserts zero data by a deficit and thus generates a normal FFT data group (step S26). The FFT data group determined as being abnormal in step S25 is subjected to the window function before zero data is added. For this reason, even when zero data is inserted into the FFT data group, data discontinuity does not occur. After step S26, the frequency analyzing unit 42 causes the process to proceed to step S27 which will be described below.

In step S27, the frequency analyzing unit 42 performs a FFT calculation using the FFT data group and acquires a frequency spectrum (step S27). The spectrum curve $C_1$ illustrated in FIG. 4 may be acquired as an example of the frequency spectrum.

Next, the frequency analyzing unit 42 adds a predetermined data step width D to the data position Z and calculates a data position Z of an FFT data group of a next analysis target (step S28). Here, the data step width D preferably matches with the data step width used when the B-mode image data generating unit 51 generates the B-mode image data, but when it is desired to reduce a computation cost in the frequency analyzing unit 42, the data step width D may be set to be larger than the data step width used by the B-mode image data generating unit 51. FIG. 13 illustrates an example in which the data step width D is 15.

Thereafter, the frequency analyzing unit 42 determines whether or not the data position Z is larger than a last data position $Z_{max}$ (step S29). Here, the last data position $Z_{max}$ may be set to a data length of the acoustic ray LD or may be set to a data position corresponding to a lower end of a region of interest. Here, when it is determined that the data position Z is larger than the last data position $Z_{max}$ (Yes in step S29), the frequency analyzing unit 42 increases the acoustic ray number L by one (1) (step S30). However, when it is determined that the data position Z is the last data position $Z_{max}$ or less (No in step S29), the frequency analyzing unit 42 causes the process to return to step S23. In the above-described way, the frequency analyzing unit 42 performs the FFT calculation on FFT data groups which are equal in number to $[\{(Z_{max}-Z_0)/D\}+1](=K)$ with respect to one acoustic ray LD. Here, [X] represents a maximum integer that does not exceed X.

Here, when the acoustic ray number L increased in step S30 is larger than a last acoustic ray number $L_{max}$ (Yes in step S31), the frequency analyzing unit 42 causes the process to return to the main routine illustrated in FIG. 10. However, when the acoustic ray number L increased in step S30 is the last acoustic ray number $L_{max}$ or less (No in step S31), the frequency analyzing unit 42 causes the process to return to step S22.

In this way, the frequency analyzing unit 42 performs the FFT calculations K times on each of $(L_{max}-L_0+1)$ acoustic rays. For example, the last acoustic ray number $L_{max}$ may be assigned to the last acoustic ray received by the transmitting-receiving unit 3 or may be assigned to the acoustic ray corresponding to either of left and right boundaries of a region of interest. Hereinafter, the total number $(L_{max}-L_0+1) \times K$ of FFT calculations which the frequency analyzing unit 42 performs all acoustic rays is referred to as P.

Subsequent to the frequency analysis process of step S8 described above, the approximating unit 431 performs regression analysis on the P frequency spectrums calculated by the frequency analyzing unit 42 as the approximate process and extracts the pre-correction feature amount (step S9). The straight line $L_1$ illustrated in FIG. 4 is a regression line corresponding to a linear expression to which the pre-correction feature amount extracted by the approximating unit 431 is assigned.

Thereafter, the attenuation correcting unit 432 performs the attenuation correction process on the pre-correction feature amount extracted by the approximating unit 431 (step S10). The attenuation correcting unit 432 calculates the feature amount of the frequency spectrum by obtaining the data position Z based on a sampling frequency of data and substituting the data position Z to the reception depth z of Formulas (2) to (4). As a result, for example, a straight line corresponding to a linear expression (see Formula (5)) in which the straight line $L_1$ illustrated in FIG. 5 is corrected is obtained. A concrete example of a calculation performed by the attenuation correcting unit 432 will be described. Here, when a sampling frequency of data is 50 MHz, a data sampling time interval is 1/50 (MHz)=20 (nsec). Here, when the speed of sound is 1530 (m/sec), a data sampling distance interval is 1530 (m/sec)×20 (nsec)/2 (=0.0153 (mm)). Here, when a data step number from first data of an acoustic ray LD up to a data position of a FFT data group of a processing target is k, the data position Z of 0.0153 k (mm) is obtained.

By performing the attenuation correction in the above-described way, signal intensity decreases due to influence of attenuation in a region having a large reception depth, it is possible to suppress an image from being darkened and obtain an image having uniform brightness on an entire screen.

Next, the feature amount image data generating unit 52 generates feature amount image data indicating visual information corresponding to the feature amount extracted by the feature amount extracting unit 43 (step S11).

Figure 14:
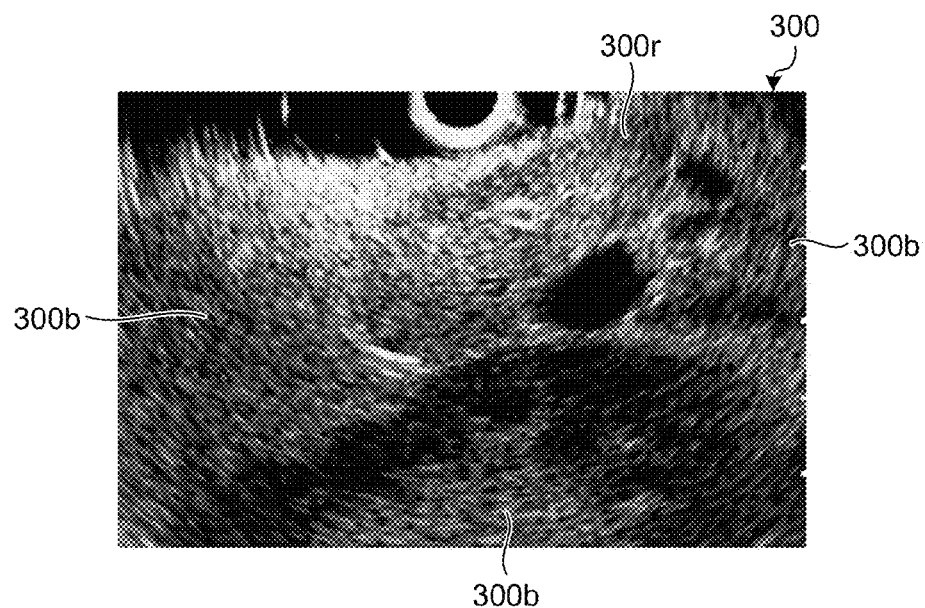
FIG. 14 is a diagram illustrating a display example of a feature amount image displayed by the display unit of the ultrasonic observation apparatus according to the first embodiment of the present invention.
Figure 15:
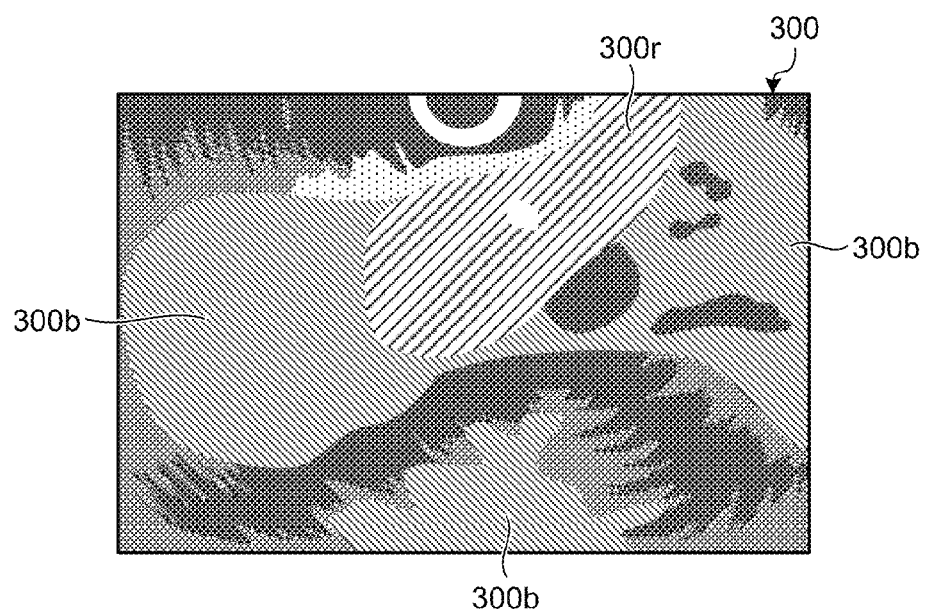
FIG. 15 is a diagram schematically illustrating an image illustrated in FIG. 14 in black and white.

Thereafter, the display unit 7 displays the feature amount image generated by the feature amount image data generating unit 52 (step S12). FIG. 14 is a diagram illustrating the feature amount image displayed by the display unit 7. FIG. 15 is a diagram schematically illustrating an image illustrated in FIG. 14 in black and white. In feature amount images 300 illustrated in FIGS. 14 and 15, hues of regions that differ in the size of a scatterer, that is, hues of regions corresponding to abnormal tissue are displayed in red (a region 300r of FIG. 15), whereas a hue of a region corresponding to normal tissue is displayed in blue (a blue region 300b of FIG. 15). It is obvious that, in FIG. 15, the red region 300r and the blue region 300b are not displayed in a single color. For example, the red region 300r is a region in which pixels having a color close to red are collected. Similarly, the blue region 300b is a region in which pixels having a color close to blue are collected. In the feature amount images 300, regions that differ in the acoustic impedance ratio or the density of scatterers are the same in hue but different in brightness from each other. Particularly, in the feature amount images 300, a portion corresponding to a vascular channel or noise is displayed in black in an unrecognizable form. According to the feature amount images 300, it is possible to understand the distribution of the acoustic impedance ratio or the density of scatterers (density) and the distribution of the size of the scatterer based on a combination of brightness and a hue. Thus, if the feature amount image is generated using a plurality of feature amounts, there is an advantage of obtaining much information at a time. The slope a or the intercept b may be associated with a hue, and the central frequency intensity c may be associated with brightness and/or chroma.

Through the above-described process, the ultrasonic observation apparatus 1 ends a series of processes. The ultrasonic observation apparatus 1 may periodically repeat the process of steps S1 to S12.

According to the first embodiment of the present invention described above, the feature amount image is generated on the frequency spectrum approximated by the polynomial such that two spectrum intensities respectively corresponding to two frequencies included in the polynomial are associated with different visual information. Thus, the feature amount image can be generated based on information of the frequency spectrum having a characteristic according to the tissue characterization. Thus, it is possible to display a vascular channel or noise in tissue of an observation target to be distinguished from another tissue, and it is possible to clearly display the difference in the tissue characterization.

Further, according to the first embodiment, the B-mode image data is generated based on the signal which has been subjected to STC correction in which amplification is performed at the gain according to the reception depth. In addition, after amplification correction of offsetting influence of STC correction and making the gain constant is performed, the frequency spectrum is calculated to extract the pre-correction feature amount, the feature amount of the frequency spectrum is extracted by executing the attenuation correction on the extracted pre-correction feature amount, and the feature amount image data which indicates the visual information corresponding to the extracted feature amount is generated. Thus, influence of attenuation accompanying transmission of an ultrasonic wave in the feature amount image data is excluded, and it is unnecessary to separately transmit a signal for a B-mode image and a signal for a feature amount image. Thus, it is possible to properly exclude influence of attenuation accompanying transmission of an ultrasonic wave, and it is possible to prevent a frame rate of image data generated based on a received ultrasonic wave from being lowered.

Furthermore, according to the first embodiment, the feature amount image is displayed using the feature amount of the frequency spectrum which has been properly subjected to the attenuation correction, and thus the user can clearly recognize the difference in the tissue characterization.

In addition, according to the first embodiment, a hue associated with a function of a difference or a ratio between an intercept and specific spectrum intensity is used as the first visual information, and brightness or chroma associated with an intercept or specific spectrum intensity is used as the second visual information. Thus, the feature amount image can be generated based on the size of a scatterer in a tissue and the difference in the acoustic impedance ratio or the density of scatterers between a scatterer and a peripheral material. Thus, it is possible to identify the tissue characterization. As a result, the user can appropriately use the feature amount image as a guide of invasion depth diagnosis, progress level diagnosis (for example, distinguishing of vascular invasion), or centesis.

As a modification of the first embodiment, the control unit 9 may perform the amplification correction process in the amplification correcting unit 41 and the attenuation correction process in the attenuation correcting unit 432 together. For this process, the amplification correction process in step S6 of FIG. 10 is not performed, and a definition of an attenuation amount of the attenuation correction process in step S10 of FIG. 10 is changed as in the following Formula (6):

$$A' = 2\alpha z f + \gamma(z) \quad (6)$$

Here, γ(z) at a right side represents a difference between gains β and $β_0$ in the reception depth z and is represented by the following formula (7):

$$γ(z)=-\{(β_{th}-β_0)/z_{th}\}z+β_{th}-β_0 (z≤z_{th}) \quad (7)$$

$$γ(z)=0 (z>z_{th}) \quad (8)$$

Figure 16:
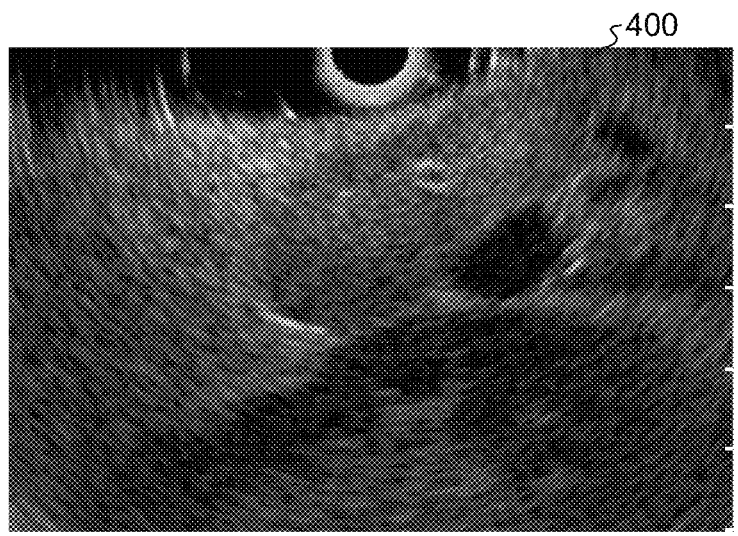
FIG. 16 is a diagram illustrating a display example (a second example) of a feature amount image displayed by a display unit of an ultrasonic observation apparatus according to a second embodiment of the present invention.
Figure 17:
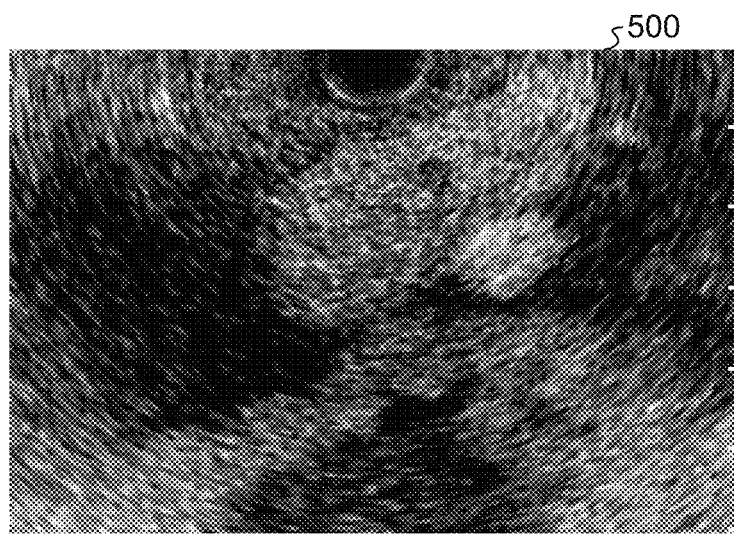
FIG. 17 is a diagram illustrating a display example (a third example) of the feature amount image displayed by the display unit of the ultrasonic observation apparatus according to the second embodiment of the present invention.

Further, in the first embodiment, when the feature amount image is generated, a single feature amount may be associated with the visual information. FIG. 16 is a diagram illustrating a display example of a feature amount image generated by associating the central frequency intensity c with brightness. According to a feature amount image 400 illustrated in FIG. 16, it is possible to understand the acoustic impedance ratio or the distribution in the density of scatterers. FIG. 17 is a diagram illustrating a display example of a feature amount image generated by associating the slope a with brightness. According to a feature amount image 500 illustrated in FIG. 17, it is possible to understand the distribution in the size of a scatterer. As described above, it is possible to understand tissue characterization according to a characteristic of an individual feature amount through a feature amount image using a single feature amount.

In addition, the ultrasonic observation apparatus 1 may have a function of switching and displaying a plurality of types of feature amount images (for example, the feature amount images 300, 400, and 500 illustrated in FIGS. 14 to 17) that differ from each other in an association between the feature amount and the visual information. In this case, for example, a use method in which a feature amount image using a plurality of feature quantities by screening positioning is first displayed on the display unit 7, and then a feature amount image using a single feature amount is used on a portion in which the observer has found abnormality is considered. In this way, it is possible to use a plurality of feature amount images through switching, and thus the user can more strictly evaluate tissue characterization of an abnormal portion.

Further, the feature amount image data generating unit 52 may generate the feature amount image data by mixing the B-mode image data with color image data at a predetermined ratio. Further, the feature amount image data generating unit 52 may generate the feature amount image data by replacing a region of interest with color image data.

Furthermore, an area between a frequency spectrum curve and a frequency axis (for example, an f axis in FIG. 4) in a frequency band $f_{LOW}>f>f_{HIGH}$ may be used as a feature amount.

Second Embodiment

A second embodiment of the present invention differs from the first embodiment in the feature amount extracting process performed by the feature amount extracting unit. A configuration of an ultrasonic observation apparatus according to the second embodiment is the same as the configuration of the ultrasonic observation apparatus 1 according to the first embodiment. Thus, in the following description, components corresponding to the components of the ultrasonic observation apparatus 1 are denoted by the same reference numerals.

In the feature amount extracting process according to the second embodiment, first the attenuation correcting unit 432 performs the attenuation correction process on the frequency spectrum calculated by the frequency analyzing unit 42. Thereafter, the approximating unit 431 extracts the feature amount of the frequency spectrum by performing the approximate process on the frequency spectrum which has been subjected to the attenuation correction through the attenuation correcting unit 432.

Figure 18:
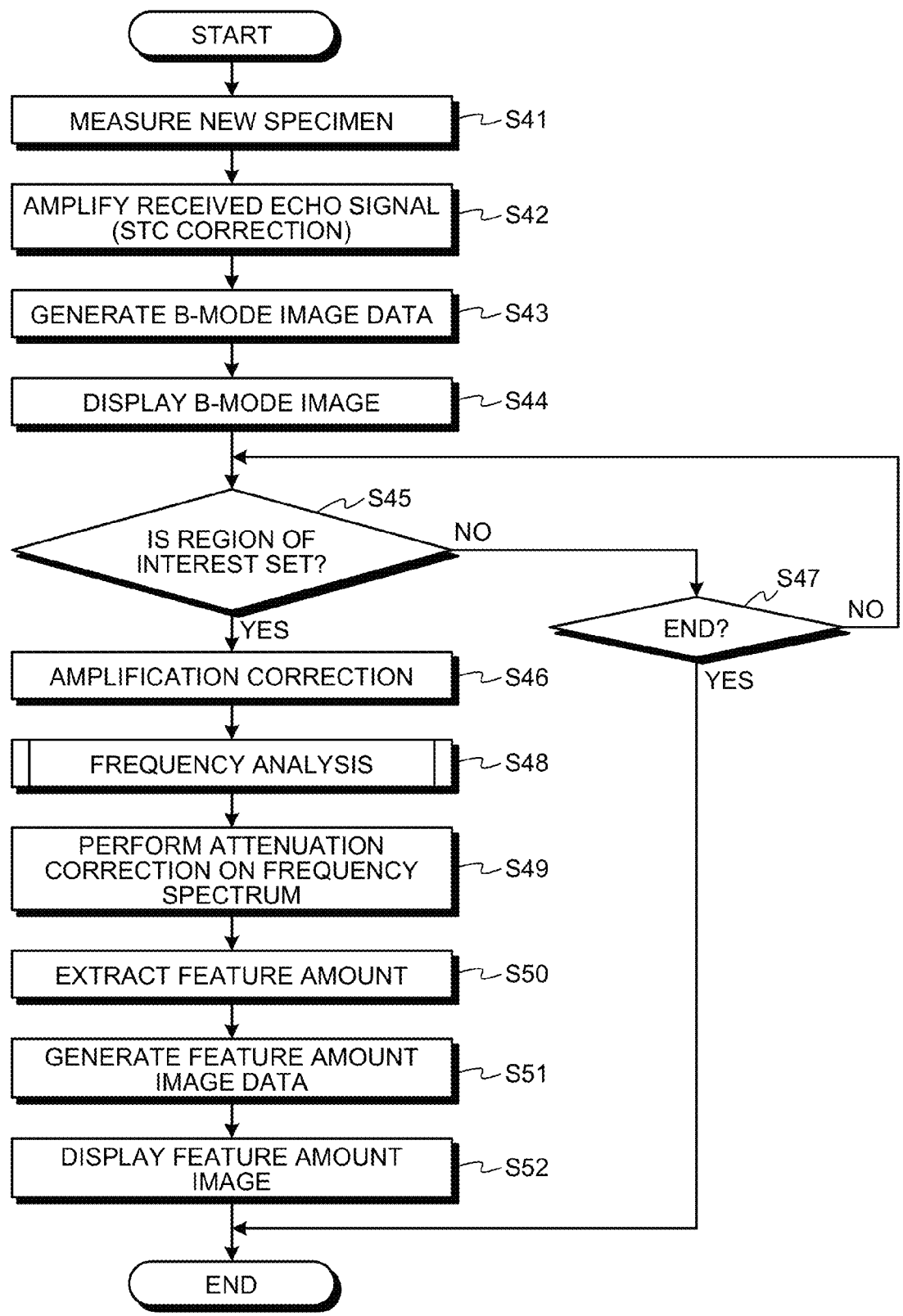
FIG. 18 is a flowchart illustrating a processing outline of the ultrasonic observation apparatus according to the second embodiment of the present invention.

FIG. 18 is a flowchart illustrating a processing outline of the ultrasonic observation apparatus 1 according to the second embodiment. The process of steps S41 to S48 in FIG. 18 sequentially corresponds to the process of steps S1 to S8 in FIG. 10.

Figure 19:
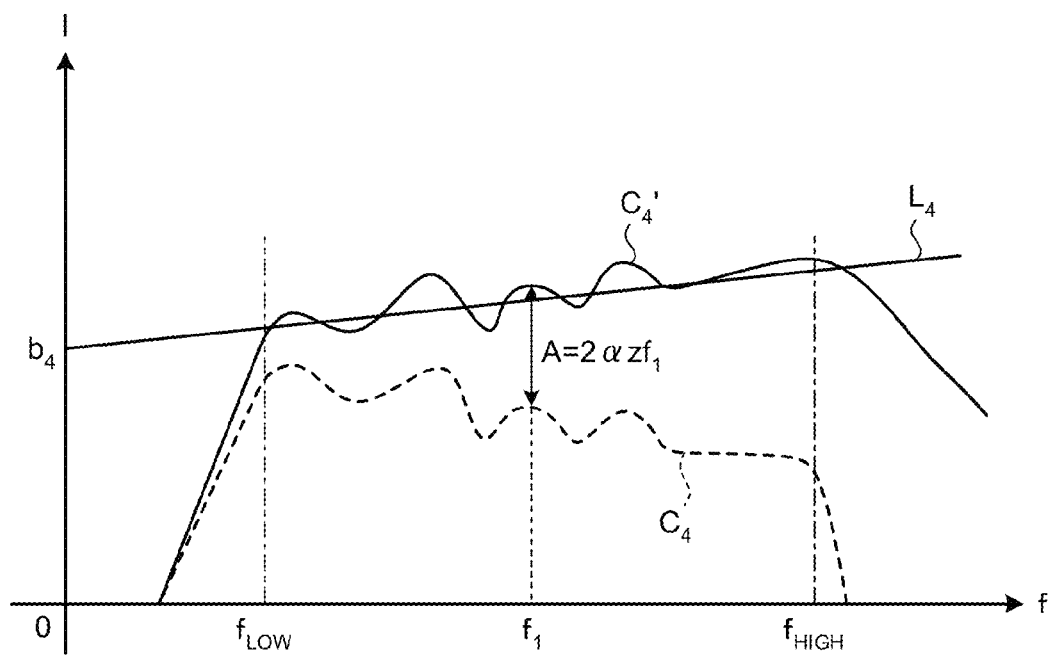
FIG. 19 is a diagram schematically illustrating an outline of an attenuation correction process performed by the ultrasonic observation apparatus according to the second embodiment of the present invention.

In step S49, the attenuation correcting unit 432 performs the attenuation correction on the frequency spectrum which the frequency analyzing unit 42 has calculated through the FFT calculation (step S49). FIG. 19 is a diagram schematically illustrating an outline of the attenuation correction process of step S49. As illustrated in FIG. 19, the attenuation correcting unit 432 obtains a new frequency spectrum curve $C_4'$ by performing correction of adding the attenuation amount A of Formula (1) to intensity I on all of frequencies f with respect to the frequency spectrum curve $C_4$. As a result, it is possible to obtain a frequency spectrum in which contribution of attenuation accompanying transmission of an ultrasonic wave is reduced.

Thereafter, the approximating unit 431 extracts the feature amount of the frequency spectrum by performing the regression analysis on all of the frequency spectrums which have been subjected to the attenuation correction through the attenuation correcting unit 432 (step S50). Specifically, the approximating unit 431 calculates the slope a, the intercept b, and the central frequency intensity c of the linear expression through the regression analysis. A straight line $L_4$ illustrated in FIG. 19 is a regression line (an intercept $b_4$) obtained by performing the feature amount extracting process on the frequency spectrum curve $C_4'$ in step S50.

The process of steps S51 and S52 sequentially corresponds to the process of steps S11 and S12 of FIG. 10.

According to the second embodiment of the present invention described above, the feature amount image is generated on the frequency spectrum approximated by the polynomial such that two spectrum intensities respectively corresponding to two frequencies included in the polynomial are associated with different visual information. Thus, the feature amount image can be generated based on information of the frequency spectrum having a characteristic according to the tissue characterization. Thus, it is possible to display a vascular channel or noise in tissue of an observation target to be distinguished from another tissue, and it is possible to clearly display the difference in the tissue characterization.

Further, according to the second embodiment, the B-mode image data is generated based on the signal which has been subjected STC correction in which amplification is performed at the gain according to the reception depth. In addition, the frequency spectrum is calculated after amplification correction of offsetting influence of STC correction and making the gain constant regardless of the reception depth is performed, the feature amount is extracted after the attenuation correction is executed on the frequency spectrum, and the feature amount image data which indicates the visual information corresponding to the extracted feature amount is generated. Thus, influence of attenuation accompanying transmission of an ultrasonic wave in the feature amount image data is excluded, and it is unnecessary to separately transmit a signal for a B-mode image and a signal for a feature amount image. Thus, similarly to the first embodiment, it is possible to properly exclude influence of attenuation accompanying transmission of an ultrasonic wave, and it is possible to prevent a frame rate of image data generated based on a received ultrasonic wave from being lowered.

Furthermore, according to the second embodiment, the feature amount image is displayed using the feature amount of the frequency spectrum which has been properly subjected to the attenuation correction, and thus the user can clearly recognize the difference in the tissue characterization.

Further, in the second embodiment, the amplification correction process in step S46 of FIG. 18 may not be performed, and an attenuation amount when the attenuation correction of the frequency spectrum is performed in step S49 of FIG. 18 may be processed as A' of Formula (6).

Third Embodiment

Figure 20:
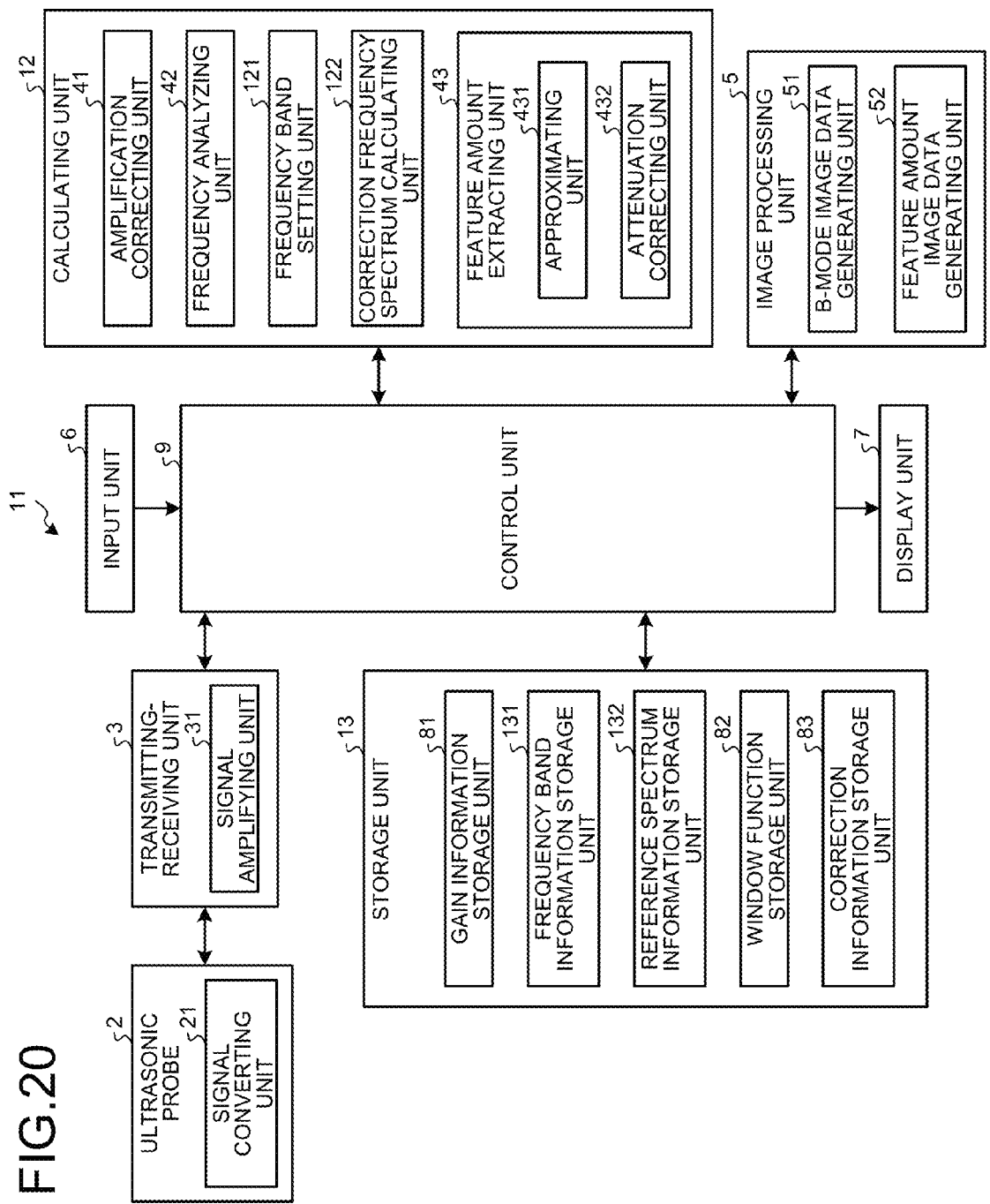
FIG. 20 is a block diagram illustrating a configuration of an ultrasonic observation apparatus according to a third embodiment of the present invention.

FIG. 20 is a block diagram illustrating a configuration of an ultrasonic observation apparatus according to a third embodiment of the present invention. An ultrasonic observation apparatus 11 illustrated in FIG. 20 differs from the ultrasonic observation apparatus 1 according to the first embodiment in a configuration of a calculating unit and a storage unit. In the following description, components corresponding to the components of the ultrasonic observation apparatus 1 are denoted by the same reference numerals.

A calculating unit 12 includes an amplification correcting unit 41, a frequency analyzing unit 42, a frequency band setting unit 121 that sets a frequency band used when the frequency spectrum calculated by the frequency analyzing unit 42 is approximated, a correction frequency spectrum calculating unit 122 that calculates the correction frequency spectrum by correcting the frequency spectrum calculated by the frequency analyzing unit 42 based on a predetermined reference spectrum stored in a storage unit 13, and a feature amount extracting unit 43 that extracts the feature amount of the correction frequency spectrum calculated by the correction frequency spectrum calculating unit 122.

The frequency band setting unit 121 sets a frequency band with reference to a frequency band table (which will be described later) stored in the storage unit 13. The reason of changing the setting of the frequency band for each reception depth as described above is because an ultrasonic wave is attenuated as fast as a high-frequency component, and thus an echo signal received from a portion having a large reception depth is likely to lose valid information of a high-frequency component and include invalid information. In this regard, in the third embodiment, a frequency band is set such that as the reception depth increases, a bandwidth decreases, and a maximum frequency decreases.

The correction frequency spectrum calculating unit 122 calculates a correction frequency spectrum by calculating a difference between a reference spectrum and a frequency spectrum for each reception depth with reference to reference spectrum information (which will be described later) stored in the storage unit 13. As described above, correction of a frequency spectrum is performed for each reception depth due to the same reason as in the setting of the frequency band.

The feature amount extracting unit 43 includes an approximating unit 431 that calculates the feature amount (the pre-correction feature amount) of the correction frequency spectrum by performing the approximate process on the correction frequency spectrum calculated by the correction frequency spectrum calculating unit 122, and an attenuation correcting unit 432 that extracts the feature amount of the frequency spectrum by performing the attenuation correction on the pre-correction feature amount calculated by the approximating unit 431.

The storage unit 13 includes a frequency band information storage unit 131 that stores frequency band information decided according to a reception depth of an ultrasonic wave and a reference spectrum information storage unit 132 that stores reference spectrum information according to a reception depth of an ultrasonic wave, in addition to the gain information storage unit 81, a window function storage unit 82, and a correction information storage unit 83.

Figures 21, 22:
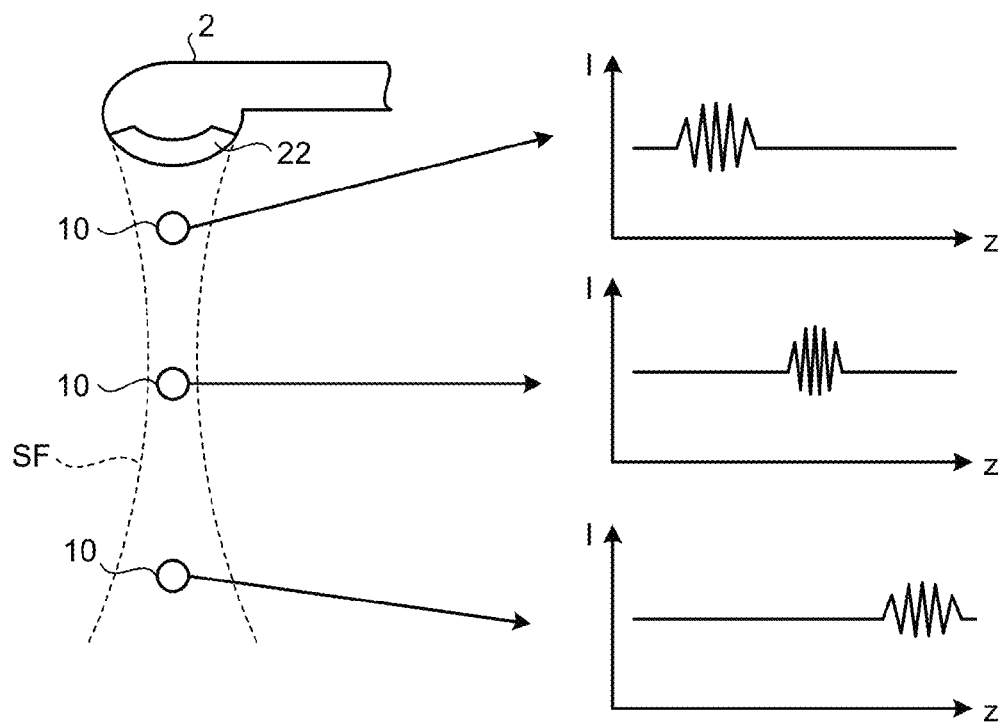
FIG. 21 is a diagram schematically illustrating a frequency band table stored in the ultrasonic observation apparatus according to the third embodiment of the present invention.
FIG. 22 is a diagram schematically illustrating an outline of a process of generating a reference spectrum stored in the ultrasonic observation apparatus according to the third embodiment of the present invention.

FIG. 21 is a diagram schematically illustrating a frequency band table serving as the frequency band information stored in the frequency band information storage unit 131. A frequency band table 700 illustrated in FIG. 21 represents a minimum frequency ($f_{LOW}$) and a maximum frequency ($f_{HIGH}$) for each reception depth of an ultrasonic wave. In the frequency band table 700, as the reception depth increases, a bandwidth $f_{HIGH}$–$f_{LOW}$ decreases, and maximum frequency $f_{HIGH}$ decreases. Further, in the frequency band table 700, when the reception depth is relatively small (2 to 6 cm in FIG. 21), influence of attenuation is small, and thus the frequency band does not change. On the other hand, when the reception depth is relatively large (8 to 12 cm in FIG. 21), influence of attenuation becomes large, and thus the bandwidth f HIGH $f_{LOW}$ decreases and moves to a low frequency side. Using the frequency band table 700, it is possible to extract a signal having valid information and generate an image based on the extracted signal. Further, the frequency band table 700 is individually set for each type (model) of the ultrasonic probe 2.

The reference spectrum information storage unit 132 stores a frequency spectrum (hereinafter, referred to as a "reference spectrum") calculated based on an echo signal reflected from a predetermined reference reflector and acquired as frequency information in the reference reflector. For example, the reference reflector is an ideal reflector that does not scatter, absorb, or transmit an ultrasonic wave. Further, the reference spectrum is calculated for each type of the ultrasonic probe 2 and for each reception depth of the ultrasonic signal. Here, the reason of calculating reference spectrums on different ultrasonic probes 2 is because a transducer and a waveform of a transmission wave differ according to the type of ultrasonic probe 2. The reference reflector may not be a reflector which is ideal in the above-described meaning.

FIG. 22 is a diagram schematically illustrating an outline of a process of generating the reference spectrum. As illustrated in FIG. 22, a transducer 22 disposed in the ultrasonic probe 2 forms an acoustic field SF which is substantially symmetric to a moving direction (a vertical direction in FIG. 22) of an ultrasonic wave centering on a focus point. FIG. 22 illustrates a relation between the reception depth z and the intensity I of each of echo signals acquired by the ultrasonic probe 2 when reference reflectors 10 are arranged on three points including the focus point. Here, when the reference spectrum is calculated, the frequency analyzing unit 42 performs the frequency analysis using intensity data of the echo signal reflected from the reference reflector 10 and calculates the reference spectrum, and stores the calculation result in the reference spectrum information storage unit 132.

Figure 23:
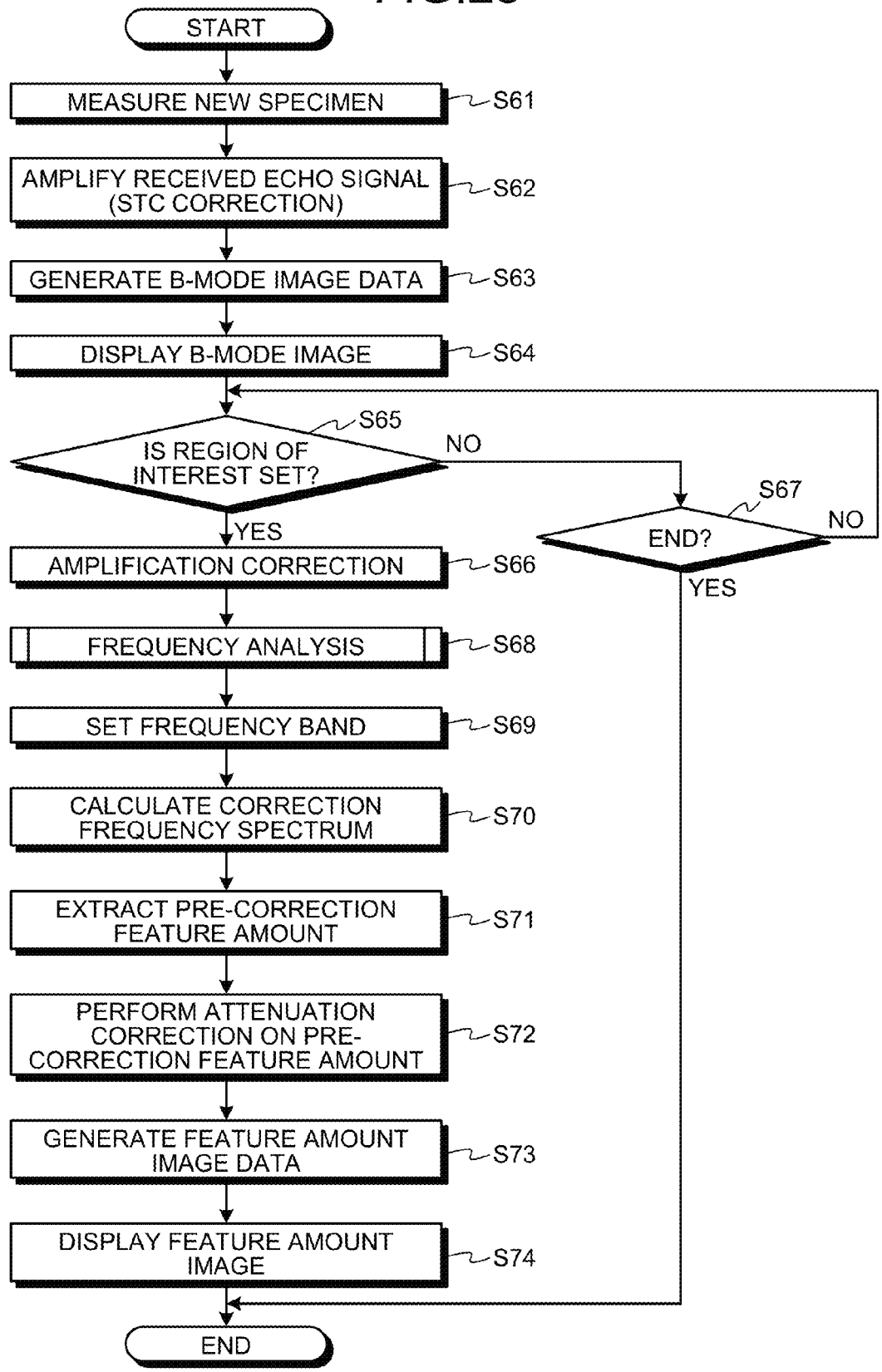
FIG. 23 is a flowchart illustrating an outline of a process performed by a frequency analyzing unit of the ultrasonic observation apparatus according to the third embodiment of the present invention.

FIG. 23 is a flowchart illustrating a processing outline of the ultrasonic observation apparatus 11 having the above-described configuration. The process of steps S61 to S68 in FIG. 23 sequentially corresponds to the process of steps S1 to S8 described with reference to FIG. 10.

After the frequency analysis process of step S68, the frequency band setting unit 121 sets a frequency band for each reception depth of an ultrasonic wave with reference to the frequency band table 700 stored in the frequency band information storage unit 131 (step S69). The process of the frequency band setting unit 121 may be performed together with the process of the frequency analyzing unit 42 or may be performed before the process of the frequency analyzing unit 42.

Figure 24:
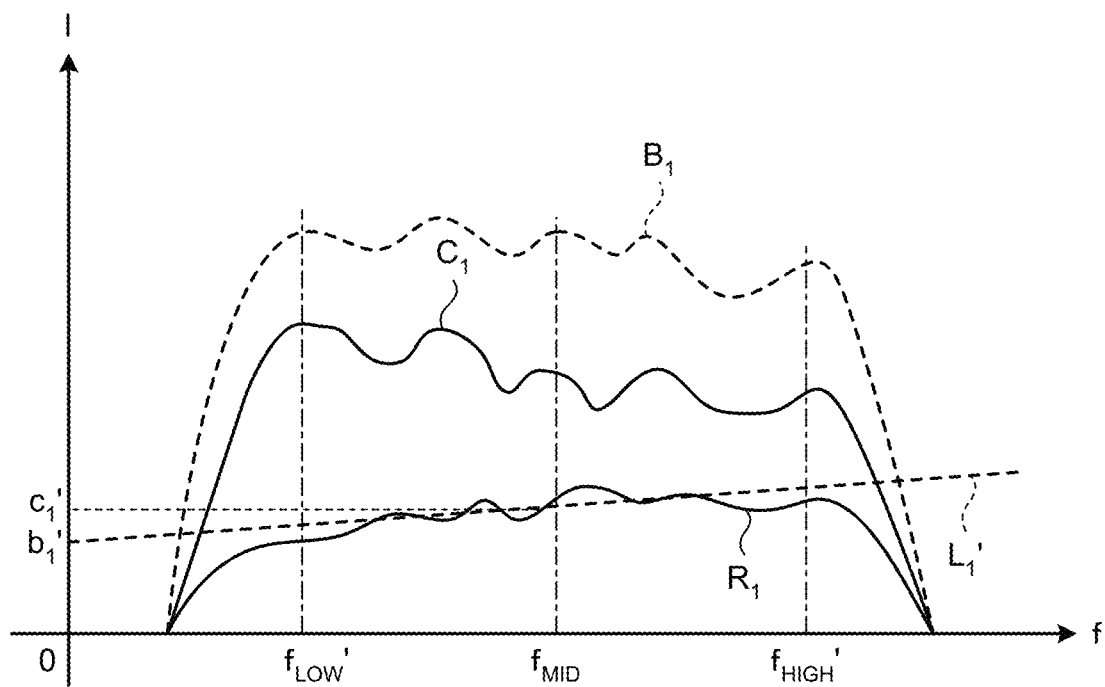
FIG. 24 is a diagram schematically illustrating outlines of a process of calculating a correction frequency spectrum and a process of extracting a feature on a frequency spectrum.

Next, the correction frequency spectrum calculating unit 122 calculates a correction frequency spectrum by reading and referring to the reception depth and the reference spectrum according to the type of the ultrasonic probe 2 from the reference spectrum information storage unit 132 and obtaining the difference between the reference spectrum and the frequency spectrum calculated by the frequency analyzing unit 42 (step S70). FIG. 24 is a diagram schematically illustrating an outline of a process of calculating the correction frequency spectrum on the frequency spectrum curve $C_1$. A curve $B_1$ illustrated in FIG. 24 illustrates a reference spectrum curve (hereinafter, referred to as a reference spectrum curve $B_1$) in the frequency spectrum curve $C_1$. The correction frequency spectrum calculating unit 122 calculates a correction frequency spectrum curve $R_1$ by obtaining the difference between the reference spectrum curve $B_1$ and the frequency spectrum curve $C_1$.

Subsequently to step S70, the approximating unit 431 extracts the pre-correction feature amount by performing the regression analysis on P frequency spectrums calculated by the frequency analyzing unit 42 as the approximate process (step S71). Specifically, the approximating unit 431 extracts the slope $a_1'$, the intercept $b_1'$, and the central frequency intensity $c_1'$ which characterize the linear expression as the pre-correction feature amount by calculating the linear expression to approximate the frequency spectrum of the frequency band $f_{LOW}' > f > f_{HIGH}'$ through the regression analysis. A straight line $L_1'$ illustrated in FIG. 24 is a regression line obtained by performing the regression analysis on the frequency spectrum curve $C_1$ in step S71. In the third embodiment, setting of the frequency band and calculation of the correction frequency spectrum are performed before the feature amount extracting process. Thus, according to the third embodiment, it is possible to extract the same feature amount (corresponding to the straight line $L_1'$) regardless of the reception depth or the type of the ultrasonic probe 2.

Thereafter, the process of steps S72 to S74 sequentially corresponds to the process of steps S10 to S12 in FIG. 10.

According to the third embodiment of the present invention described above, the feature amount image is generated on the frequency spectrum approximated by the polynomial such that two spectrum intensities respectively corresponding to two frequencies included in the polynomial are associated with different visual information. Thus, the feature amount image can be generated based on information of the frequency spectrum having a characteristic according to the tissue characterization. Thus, it is possible to display a vascular channel or noise in tissue of an observation target to be distinguished from another tissue, and it is possible to clearly display the difference in the tissue characterization.

Further, according to the third embodiment, the frequency spectrum is calculated by analyzing the frequency of the received ultrasonic wave, the frequency band used to approximate the frequency spectrum is set, the frequency spectrum is corrected based on the reference spectrum read from the storage unit that stores the reference spectrum acquired based on the frequency of the ultrasonic wave received from the reference reflector, the pre-correction feature amount is extracted by performing the approximate process on the corrected correction frequency spectrum, the feature amount is extracted by performing the attenuation correction process to reduce contribution of attenuation of the ultrasonic wave depending on the reception depth and the frequency of the ultrasonic wave on the extracted pre-correction feature amount, the feature amount image is generated based on the feature amount, and thus it is possible to generate the feature amount image by which the difference in the tissue characterization can be clearly distinguished.

Furthermore, according to the third embodiment, the attenuation correction is executed on the extracted feature amount, and thus it is possible to remove influence of attenuation accompanying transmission of an ultrasonic wave.

In addition, according to the third embodiment, the frequency band is set such that as the reception depth increases, the bandwidth decreases, and the maximum frequency decreases. Thus, even in this meaning, it is possible to remove influence of attenuation accompanying transmission of an ultrasonic wave.

Fourth Embodiment

Figure 25:
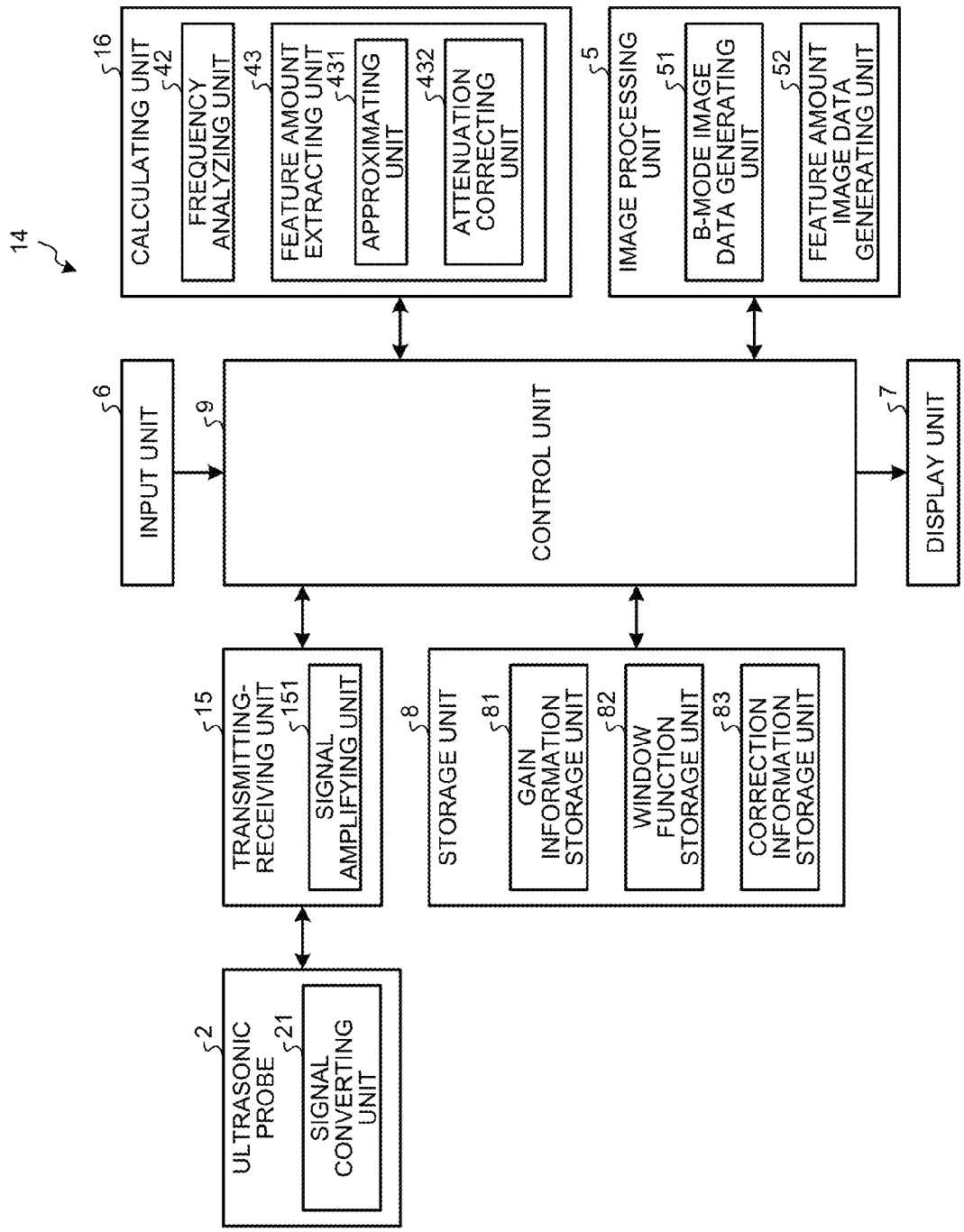
FIG. 25 is a block diagram illustrating a configuration of an ultrasonic observation apparatus according to a fourth embodiment of the present invention.

FIG. 25 is a block diagram illustrating a configuration of an ultrasonic observation apparatus according to a fourth embodiment of the present invention. An ultrasonic observation apparatus 14 illustrated in FIG. 25 performs amplification for a B-mode image and amplification for a calculation in different ways when amplifying an echo signal. Of components of the ultrasonic observation apparatus 14, components having the same function as in the ultrasonic observation apparatus 1 are denoted by the same reference numerals as the components of the ultrasonic observation apparatus 1.

Figure 26:
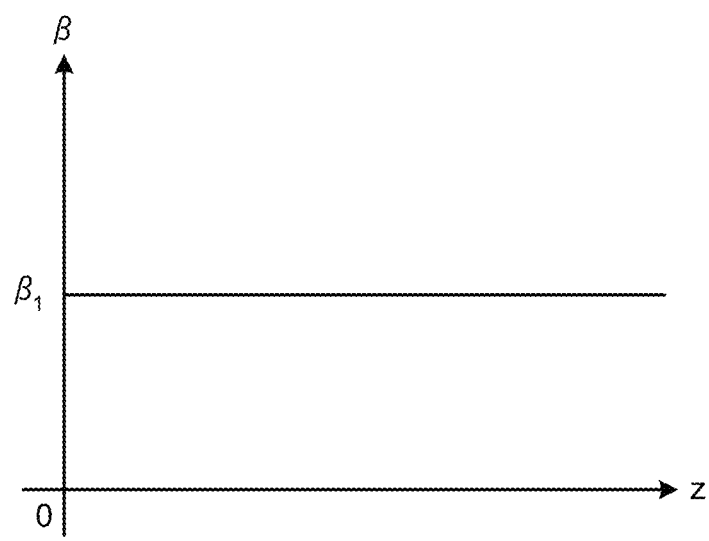
FIG. 26 is a diagram illustrating a relation between a gain and a reception depth of a calculation echo signal.

A transmitting-receiving unit 15 includes a signal amplifying unit 151 that amplifies an echo signal. The signal amplifying unit 151 amplifies an echo signal (hereinafter, referred to as a "B-mode image echo signal") which the image processing unit 5 uses to generate B-mode image data and an echo signal (hereinafter, referred to as a "calculation echo signal") which a calculating unit 16 uses to execute a calculation with different gains. Specifically, the signal amplifying unit 151 performs STC correction in which an echo signal is amplified with a higher gain as the echo signal has a larger reception depth as illustrated in FIG. 2 on the B-mode image echo signal, and performs a process of performing amplification with a constant gain ($\beta_1$) regardless of the reception depth as illustrated in FIG. 26 on the calculation echo signal. The signal amplifying unit 151 performs amplification of the B-mode image echo signal and amplification of the calculation echo signal while performing switching in units of frames or in units of lines.

The calculating unit 16 includes the frequency analyzing unit 42 and the feature amount extracting unit 43. In the fourth embodiment, since it is unnecessary to perform amplification correction before the frequency analysis process is performed, the calculating unit 16 does not include an amplification correcting unit.

The gain information storage unit 81 of the storage unit 8 stores the relation between the reception depth and the gain illustrated in FIG. 26 in addition to the relation between the reception depth and the gain illustrated in FIGS. 2 and 3.

Figure 27:
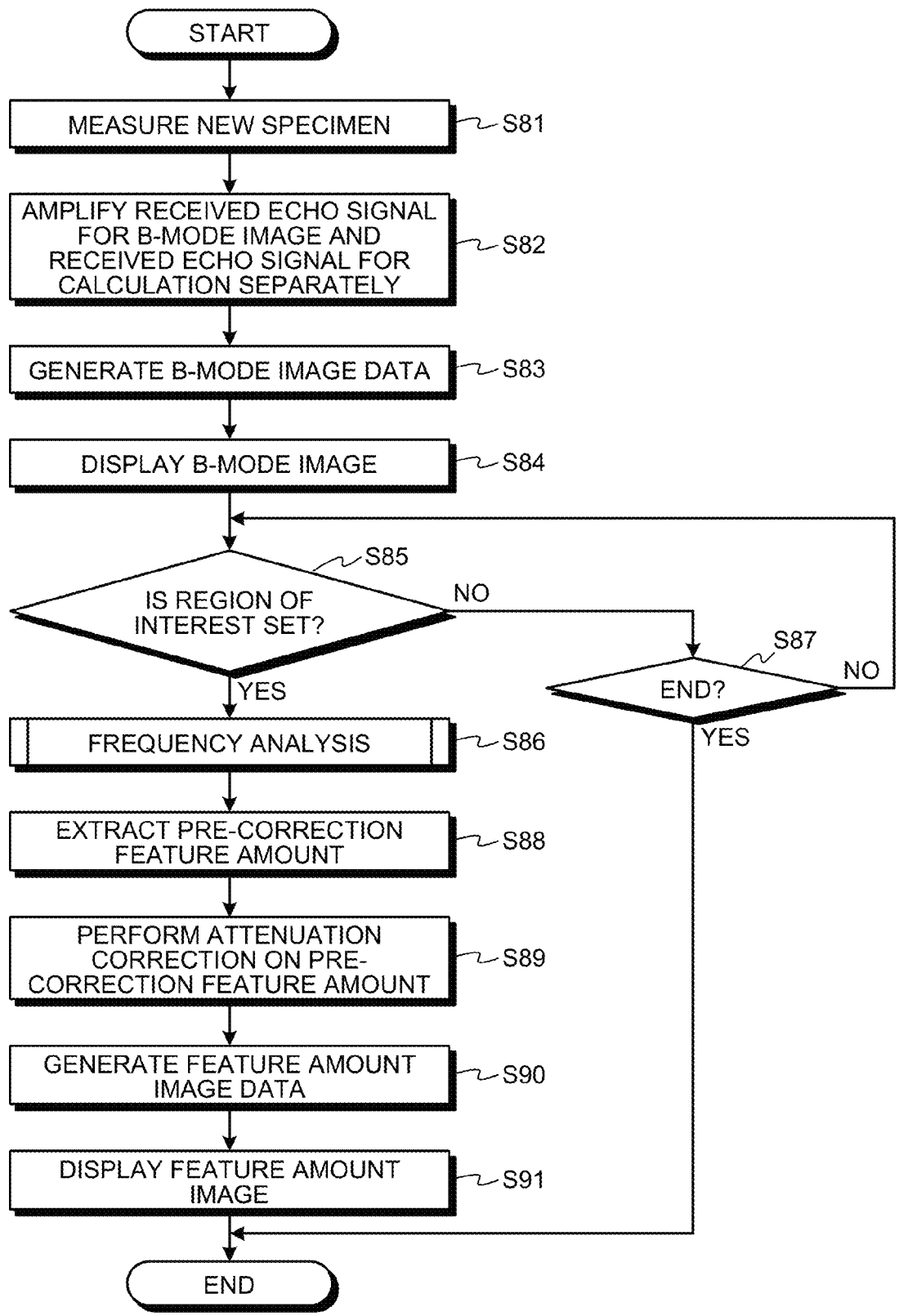
FIG. 27 is a flowchart illustrating an outline of a process performed by a frequency analyzing unit of the ultrasonic observation apparatus according to the fourth embodiment of the present invention.

FIG. 27 is a flowchart illustrating a processing outline of the ultrasonic observation apparatus 14 having the above-described configuration. Referring to FIG. 27, the ultrasonic observation apparatus 14 first measures a new specimen through the ultrasonic probe 2 (step S81).

Next, the signal amplifying unit 151 that has received an echo signal from the ultrasonic probe 2 performs an amplifying process on the echo signal for the B-mode image and an amplifying process on the echo signal for the calculation, separately while switching between the amplifying process for the B-mode image and the amplifying process for the calculation (step S82). The signal amplifying unit 151 performs amplification based on the relation between the reception depth and the gain illustrated in FIGS. 2 and 26. Further, the switching between the amplifying process for the B-mode image and the amplifying process for the calculation may be performed in units of frames or in units of lines.

Thereafter, the B-mode image data generating unit 51 generates B-mode image data using the B-mode image echo signal output from the transmitting-receiving unit 15 (step S83).

Next, the control unit 9 performs control such that a B-mode image corresponding to the B-mode image data generated by the B-mode image data generating unit 51 is displayed on the display unit 7 (step S84).

Thereafter, if a region of interest is set through the input unit 6 (Yes in step S85), the frequency analyzing unit 42 performs the frequency analysis through the FFT calculation and calculates the frequency spectrum (step S86). The frequency analysis process is the same as the frequency analysis process described in the first embodiment (see FIG. 12).

However, if the region of interest is not set in step S85 (No in step S85) and instructions to end the process are input through the input unit 6 (Yes in step S87), the ultrasonic observation apparatus 14 ends the process. However, if the region of interest is not set in step S85 (No in step S85) and the instructions to end the process are not input through the input unit 6 (No in step S87), the ultrasonic observation apparatus 14 causes the process to return to step S85.

The process of steps S88 to S91 performed subsequently to step S86 sequentially corresponds to the process of steps S9 to S12 of FIG. 10.

According to the fourth embodiment of the present invention described above, the feature amount image is generated on the frequency spectrum approximated by the polynomial such that two spectrum intensities respectively corresponding to two frequencies included in the polynomial are associated with different visual information. Thus, the feature amount image can be generated based on information of the frequency spectrum having a characteristic according to the tissue characterization. Thus, it is possible to display a vascular channel or noise in tissue of an observation target to be distinguished from another tissue, and it is possible to clearly display the difference in the tissue characterization.

Further, according to the fourth embodiment, the feature amount of the frequency spectrum is extracted such that the approximate process is performed on the frequency spectrum obtained by analyzing the frequency of the received ultrasonic wave, and then the attenuation correction process to reduce contribution of attenuation of an ultrasonic wave depending on the reception depth and the frequency of an ultrasonic wave is performed. Thus, it is possible to remove influence of attenuation accompanying transmission of an ultrasonic wave.

Hereinbefore, the embodiments for embodying the present invention have been described, but the present invention is not limited to the first to fourth embodiments.

For example, the ultrasonic observation apparatus according to the present invention may automatically determine tissue characterization of observation target tissue and display the determination result. Specifically, the ultrasonic observation apparatus determines the tissue characterization based on known specimen information in which a feature amount of a frequency spectrum previously extracted on a known specimen is associated with tissue characterization and a feature amount of a frequency spectrum extracted from observation target tissue, generates an image corresponding to the determination result, and displays the image. In this case, the feature amount extracting process performed on the known specimen is preferably the same as that performed on the observation target.

As described above, the present invention can include various embodiments within a range not departing from a technical spirit set forth in claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus that transmits an ultrasonic wave to a specimen and receives the ultrasonic wave reflected from the specimen, the ultrasonic observation apparatus comprising:
    a frequency analyzing unit that analyzes frequencies of the ultrasonic wave at a plurality of points which are respectively positioned on a plurality of acoustic rays of the received ultrasonic wave and different from each other to calculate a frequency spectrum of each of the points;
    a feature amount extracting unit that approximates a portion included in a frequency band between a first frequency and a second frequency larger than the first frequency, by a polynomial, in the frequency spectrum of each of the points calculated by the frequency analyzing unit to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum of each of the points; and
    a feature amount image data generating unit that associates any one of (a) the first spectrum intensity, (b) the second spectrum intensity, and (c) a function of a difference or a ratio between the first spectrum intensity and the second spectrum intensity, with first visual information to generate a feature amount image which visually indicates a distribution of the feature amount.

2. The ultrasonic observation apparatus according to claim 1,
    wherein the feature amount image data generating unit associates either of the remaining two other than the one of (a) to (c) associated with the first visual information, with second visual information different from the first visual information.

3. The ultrasonic observation apparatus according to claim 2,
    wherein the third frequency is a frequency included in the frequency band, and
    the fourth frequency is a frequency which is not included in the frequency band.

4. The ultrasonic observation apparatus according to claim 3,
    wherein the feature amount extracting unit approximates the frequency spectrum using a linear expression, and
    one of the first and second spectrum intensity is an intercept of the linear expression, and the other is specific spectrum intensity which is decided using a slope of the linear expression, the intercept of the linear expression, and the third frequency.

5. The ultrasonic observation apparatus according to claim 4, wherein the first visual information is a hue which is associated with a function of a difference or a ratio between the intercept and the specific spectrum intensity, and the second visual information is brightness and/or chroma which is associated with the intercept or the specific spectrum intensity.

6. The ultrasonic observation apparatus according to claim 4,
wherein the first visual information is a hue which is associated with the intercept, and
the second visual information is brightness and/or chroma which is associated with the specific spectrum intensity.

7. The ultrasonic observation apparatus according to claim 2,
further comprising an input unit that receives an input of a switching instruction signal to switch association between the first and second visual information, and the first spectrum intensity, the second spectrum intensity, the function of a difference or a ratio between the first spectrum intensity and the second spectrum intensity,
wherein the feature amount image data generating unit generates the feature amount image according to the switching instruction signal received by the input unit.

8. The ultrasonic observation apparatus according to claim 1,
wherein the feature amount extracting unit includes:
an approximating unit that approximates the frequency spectrum by the polynomial and extracts a pre-correction feature amount based on the polynomial, and
an attenuation correcting unit that performs attenuation correction on the pre-correction feature amount extracted by the approximating unit for reducing contribution of attenuation which occurs according to a reception depth and a frequency of an ultrasonic wave when the ultrasonic wave is transmitted, to extract the feature amount of the frequency spectrum.

9. The ultrasonic observation apparatus according to claim 8,
wherein the attenuation correcting unit performs larger correction as the reception depth of the ultrasonic wave increases.

10. The ultrasonic observation apparatus according to claim 8, further comprising:
a signal amplifying unit that amplifies a signal of the ultrasonic wave received from the specimen with a gain according to the reception depth;
a B-mode image data generating unit that converts an amplitude of the signal of the ultrasonic wave amplified by the signal amplifying unit into luminance to generate a B-mode image to display;
an amplification correcting unit that performs amplification correction on the signal of the ultrasonic wave amplified by the signal amplifying unit for causing the gain to be constant regardless of the reception depth; and
a control unit that causes correction by the amplification correcting unit and correction by the attenuation correcting unit to be performed together,
wherein the frequency analyzing unit analyzes the frequencies of the signal of the ultrasonic wave on which the amplification correction has been performed by the amplification correcting unit.

11. The ultrasonic observation apparatus according to claim 10,
wherein the gain monotonically increases up to a predetermined reception depth when the signal amplifying unit performs amplification.

12. The ultrasonic observation apparatus according to claim 1,
wherein the feature amount extracting unit includes:
an attenuation correcting unit that performs attenuation correction on the frequency spectrum for reducing contribution of attenuation which occurs according to a reception depth and a frequency of an ultrasonic wave when the ultrasonic wave is transmitted, and
an approximating unit that approximates the frequency spectrum corrected by the attenuation correcting unit by the polynomial and extracts the feature amount based on the polynomial.

13. The ultrasonic observation apparatus according to claim 1, further comprising:
a signal amplifying unit that amplifies a signal of the ultrasonic wave received from the specimen with a gain according to a reception depth;
a B-mode image data generating unit that converts an amplitude of the signal of the ultrasonic wave amplified by the signal amplifying unit into luminance to generate a B-mode image to display; and
an amplification correcting unit that performs amplification correction on the signal of the ultrasonic wave amplified by the signal amplifying unit for causing the gain to be constant regardless of the reception depth,
wherein the frequency analyzing unit analyzes the frequencies of the signal of the ultrasonic wave on which the amplification correction has been performed by the amplification correcting unit.

14. The ultrasonic observation apparatus according to claim 1, further comprising:
a signal amplifying unit that amplifies a reception signal of the ultrasonic wave received from the specimen; and
a B-mode image data generating unit that converts an amplitude of the reception signal amplified by the signal amplifying unit into luminance to generate a B-mode image to display,
wherein the signal amplifying unit performs amplification on a signal to be output to the B-mode image data generating unit while changing a gain according to a reception depth, and performs amplification on a signal to be output to the frequency analyzing unit with a constant gain.

15. The ultrasonic observation apparatus according to claim 14,
wherein the gain with respect to the signal to be output to the B-mode image data generating unit monotonically increases up to a predetermined reception depth.

16. The ultrasonic observation apparatus according to claim 1, further comprising:
a storage unit that stores a reference spectrum obtained based on a frequency of an ultrasonic wave received from a reference reflector;
a frequency band setting unit that sets the frequency band; and
a correction frequency spectrum calculating unit that corrects the frequency spectrum calculated by the frequency analyzing unit based on the reference spectrum stored in the storage unit to calculate a correction frequency spectrum,
wherein the feature amount extracting unit extracts the feature amount of the correction frequency spectrum calculated by the correction frequency spectrum calculating unit.

17. The ultrasonic observation apparatus according to claim 16,
wherein the storage unit stores at least the reference spectrum for each reception depth of the ultrasonic wave, and
the correction frequency spectrum calculating unit calculates the correction frequency spectrum by obtaining a difference between the reference spectrum and the frequency spectrum for each reception depth.

18. The ultrasonic observation apparatus according to claim 16,
wherein the storage unit includes a frequency band information storage unit that stores a frequency band that is decided according to a reception depth of an ultrasonic wave and decreases in a bandwidth and a maximum frequency as the reception depth increases, and
the frequency band setting unit sets the frequency band with reference to frequency band information stored in the frequency band information storage unit.

19. The ultrasonic observation apparatus according to claim 1, further comprising a display unit that displays the feature amount image.

20. An operation method of an ultrasonic observation apparatus that transmits an ultrasonic wave to a specimen and receives the ultrasonic wave reflected from the specimen, the operation method comprising:
analyzing, by a frequency analyzing unit, frequencies of the ultrasonic wave at a plurality of points which are respectively positioned on a plurality of acoustic rays of the received ultrasonic wave and different from each other to calculate a frequency spectrum of each of the points;
approximating, by a feature amount extracting unit, a portion included in a frequency band between a first frequency and a second frequency larger than the first frequency, by a polynomial, in the calculated frequency spectrum of each of the points to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum of each of the points; and
associating, by a feature amount image data generating unit, any one of (a) the first spectrum intensity, (b) the second spectrum intensity, and (c) a function of a difference or a ratio between the first spectrum intensity and the second spectrum intensity, with first visual information to generate a feature amount image which visually indicates a distribution of the feature amount.

21. A non-transitory computer readable recording medium with an executable program stored thereon, wherein the program instructs a processor to perform:
analyzing, by a frequency analyzing unit, frequencies of an ultrasonic wave at a plurality of points which are respectively positioned on a plurality of acoustic rays of the ultrasonic wave and different from each other to calculate a frequency spectrum of each of the points;
approximating, by a feature amount extracting unit, a portion included in a frequency band between a first frequency and a second frequency larger than the first frequency, by a polynomial, in the calculated frequency spectrum of each of the points to extract at least first spectrum intensity which is a value of the polynomial in a third frequency included in a domain of the polynomial and second spectrum intensity which is a value of the polynomial in a fourth frequency different from the first to third frequencies, as a feature amount of the frequency spectrum of each of the points; and
associating, by a feature amount image data generating unit, any one of (a) the first spectrum intensity, (b) the second spectrum intensity, and (c) a function of a difference or a ratio between the first spectrum intensity and the second spectrum intensity, with first visual information to generate a feature amount image which visually indicates a distribution of the feature amount.

* * * * *